(12) United States Patent
Ohara

(10) Patent No.: US 10,598,850 B2
(45) Date of Patent: Mar. 24, 2020

(54) LIGHTING UNIT

(71) Applicant: OLYUMPUS CORPORATION, Tokyo (JP)

(72) Inventor: Satoshi Ohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/183,800

(22) Filed: Nov. 8, 2018

(65) Prior Publication Data

US 2019/0094458 A1 Mar. 28, 2019

Related U.S. Application Data

(63) Continuation of application No. PCT/JP2016/065739, filed on May 27, 2016.

(51) Int. Cl.
*G02B 6/02* (2006.01)
*F21V 8/00* (2006.01)

(52) U.S. Cl.
CPC ....... *G02B 6/02038* (2013.01); *G02B 6/0008* (2013.01); *G02B 6/0208* (2013.01)

(58) Field of Classification Search
None
See application file for complete search history.

(56) References Cited

U.S. PATENT DOCUMENTS

| | | | |
|---|---|---|---|
| 6,829,411 B2 * | 12/2004 | Easley | G02B 6/262 385/31 |
| 2011/0134656 A1 | 6/2011 | Kitano | |
| 2012/0275180 A1 | 11/2012 | Button et al. | |

FOREIGN PATENT DOCUMENTS

| | | |
|---|---|---|
| JP | 2003-160734 A | 6/2003 |
| JP | 2011-120627 A | 6/2011 |
| JP | 2011-248022 A | 12/2011 |
| JP | 2013-090674 A | 5/2013 |
| JP | 2014-519140 A | 8/2014 |
| JP | 2016-049542 A | 4/2016 |

OTHER PUBLICATIONS

English translation of International Preliminary Report on Patentability dated Dec. 6, 2018 together with the Written Opinion received in related International Application No. PCT/JP2016/065739.
International Search Report dated Aug. 16, 2016 issued in PCT/JP2016/065739.
Japanese Office Action dated Oct. 23, 2019 in Japanese Patent Application No. 2018-518920.
Japanese Office Action dated Jan. 21, 2020 in Japanese Patent Application No. 2018-518920.

* cited by examiner

*Primary Examiner* — John Bedtelyon
(74) *Attorney, Agent, or Firm* — Scully, Scott, Murphy & Presser, P.C.

(57) ABSTRACT

A lighting unit includes a single core optical fiber, a light converter, and an exit end. The single core optical fiber includes an incident end and a distal end, and is configured to guide primary light, which is a laser light incident on the incident end, to the distal end. The light converter is formed inside the optical fiber, and is configured to receive the primary light guided by the optical fiber, convert optical properties of at least part of the received primary light and generate secondary light. The exit end is arranged at the distal end of the optical fiber, and is configured to emit the secondary light externally as illumination light.

20 Claims, 15 Drawing Sheets

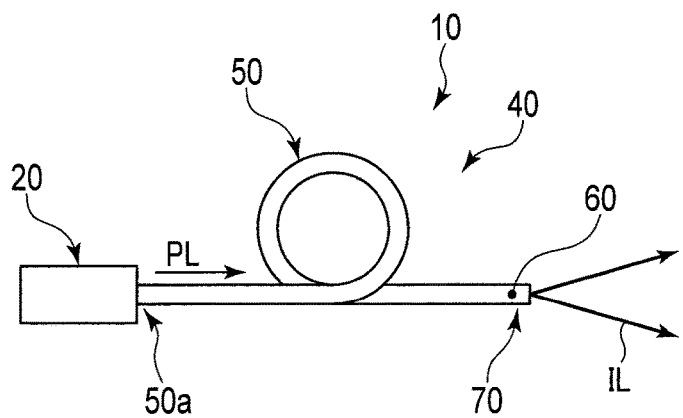
F I G. 1
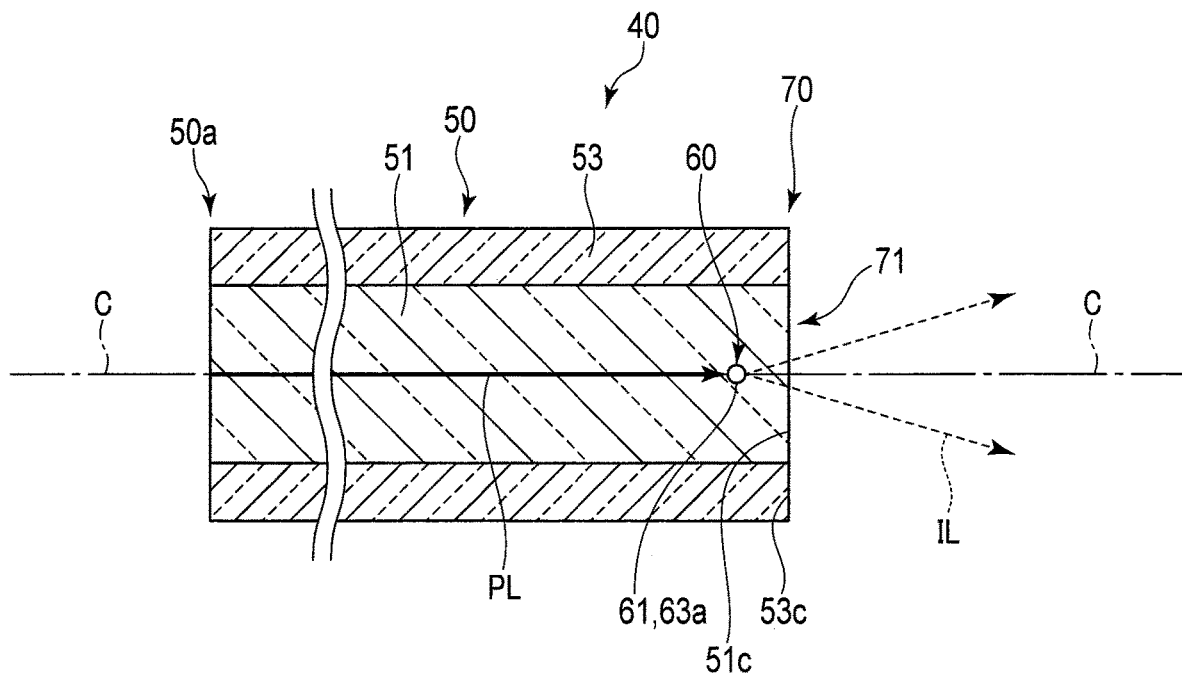
F I G. 2

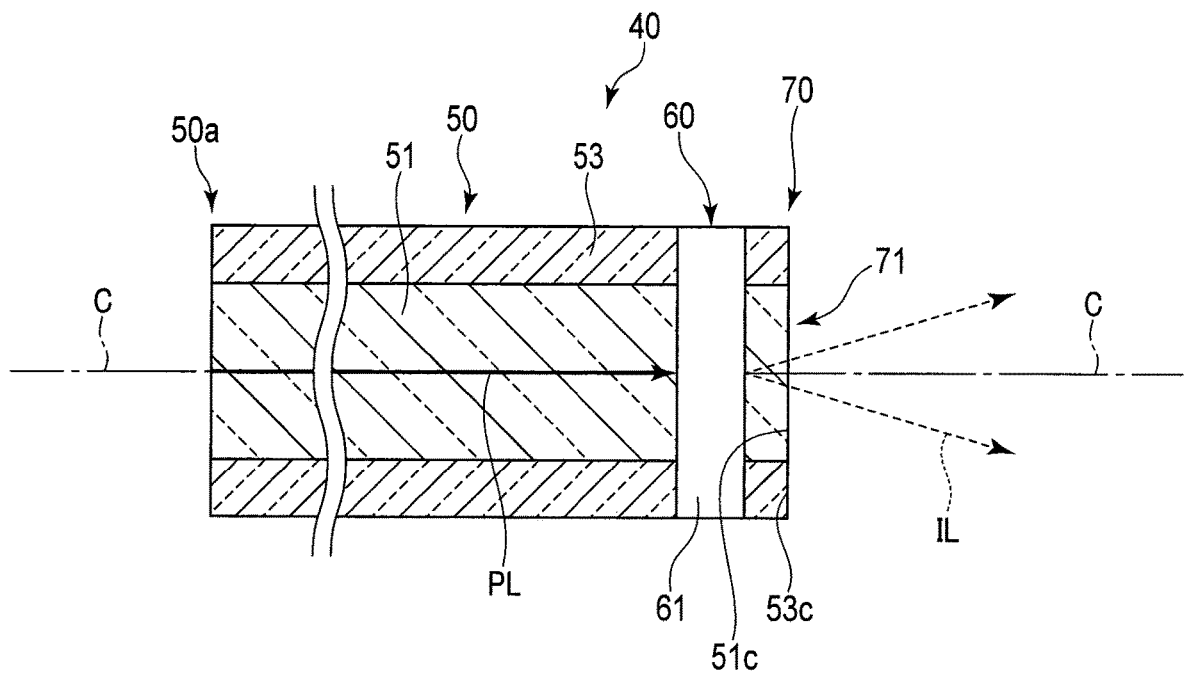
F I G. 3
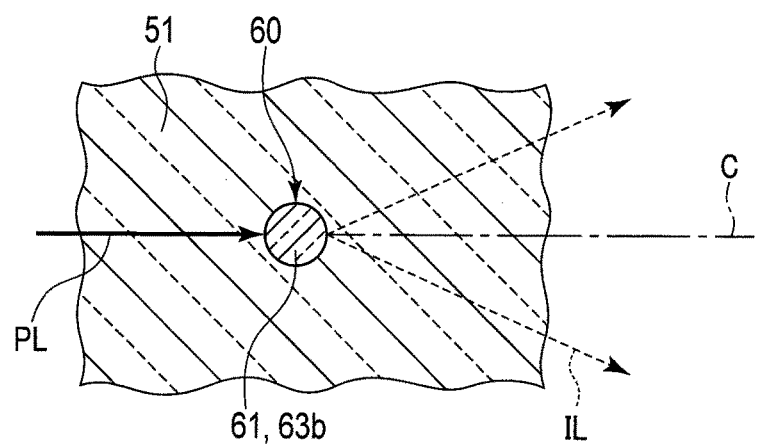
F I G. 4A

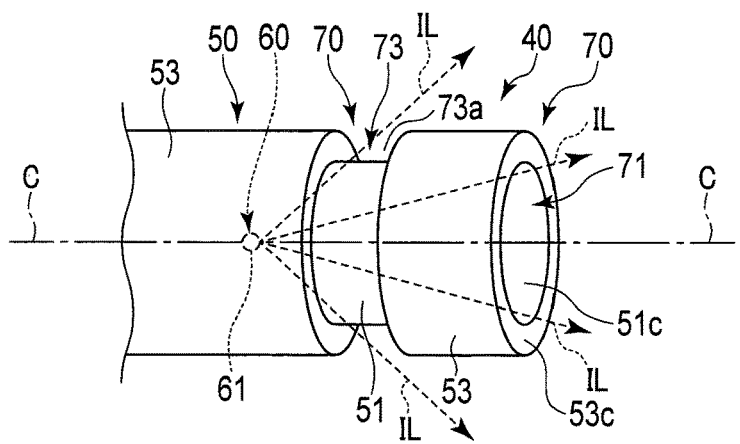
F I G. 12B
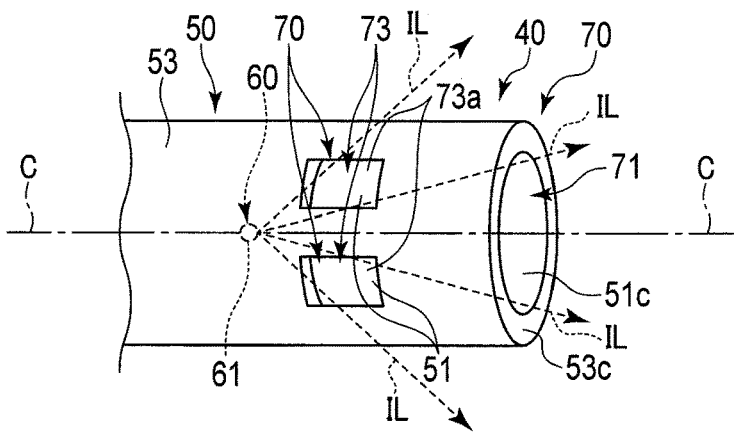
F I G. 12C
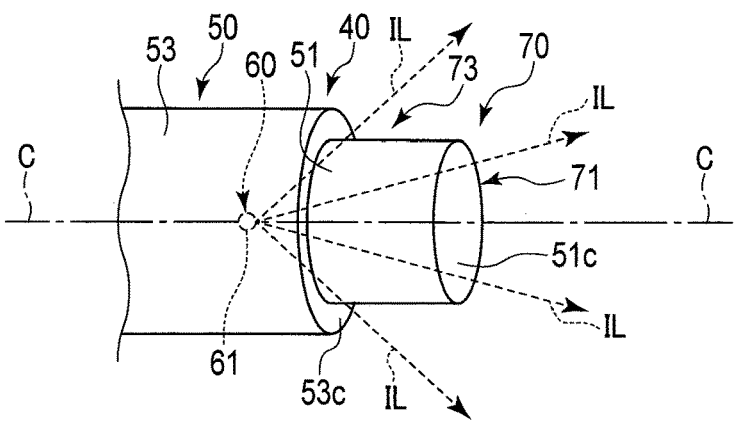
F I G. 12D

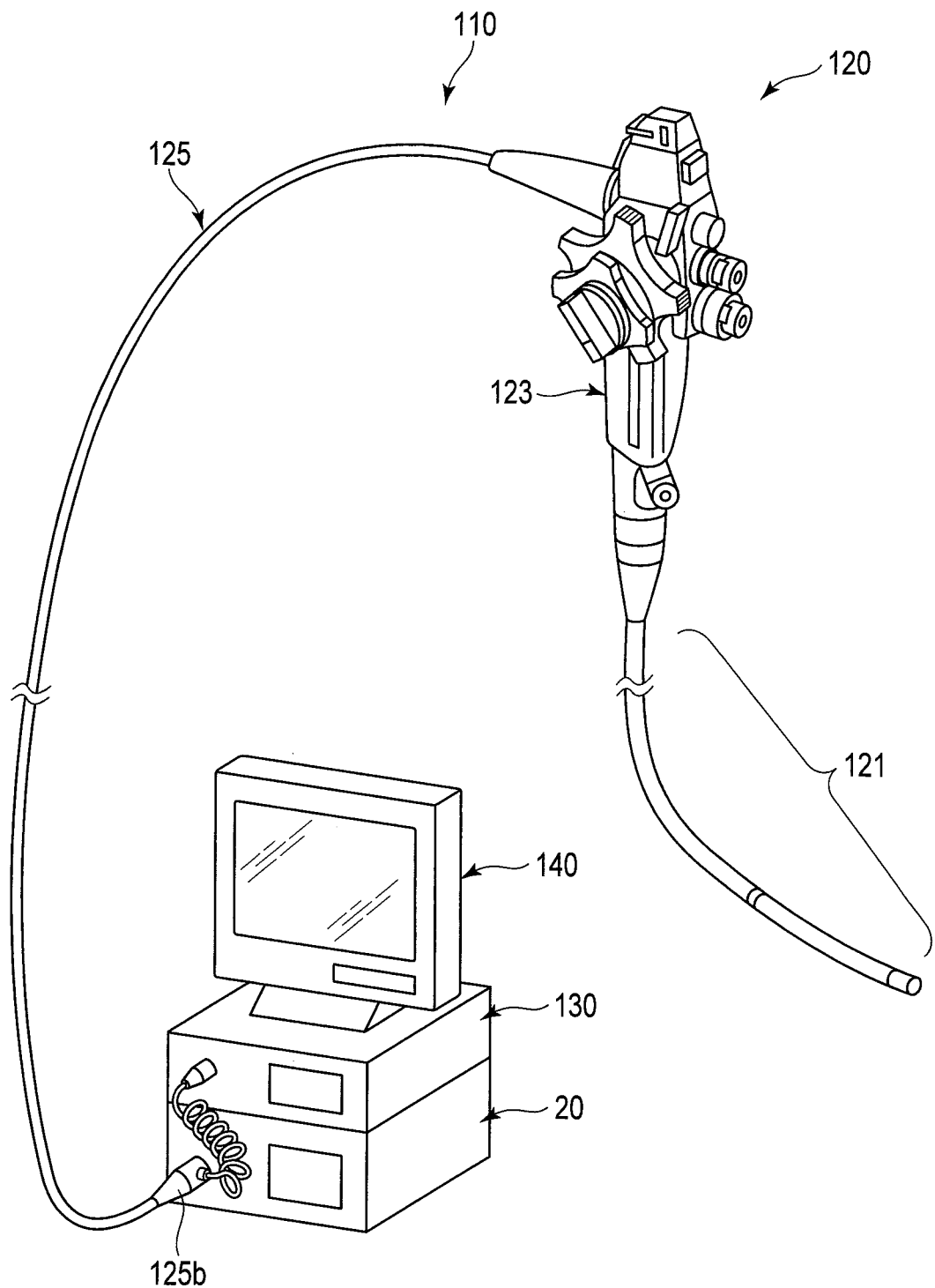
F I G. 13A

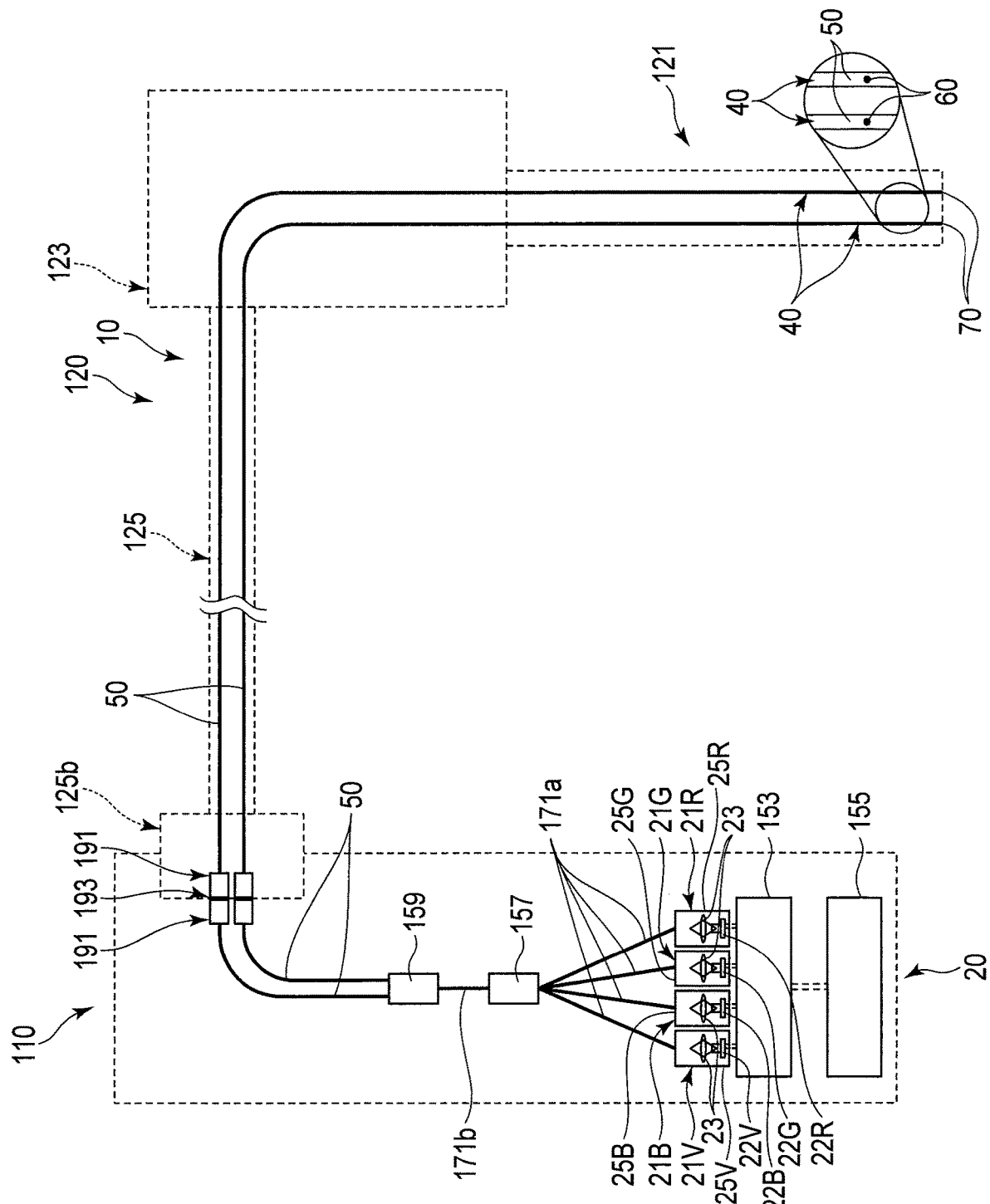
F I G. 13B

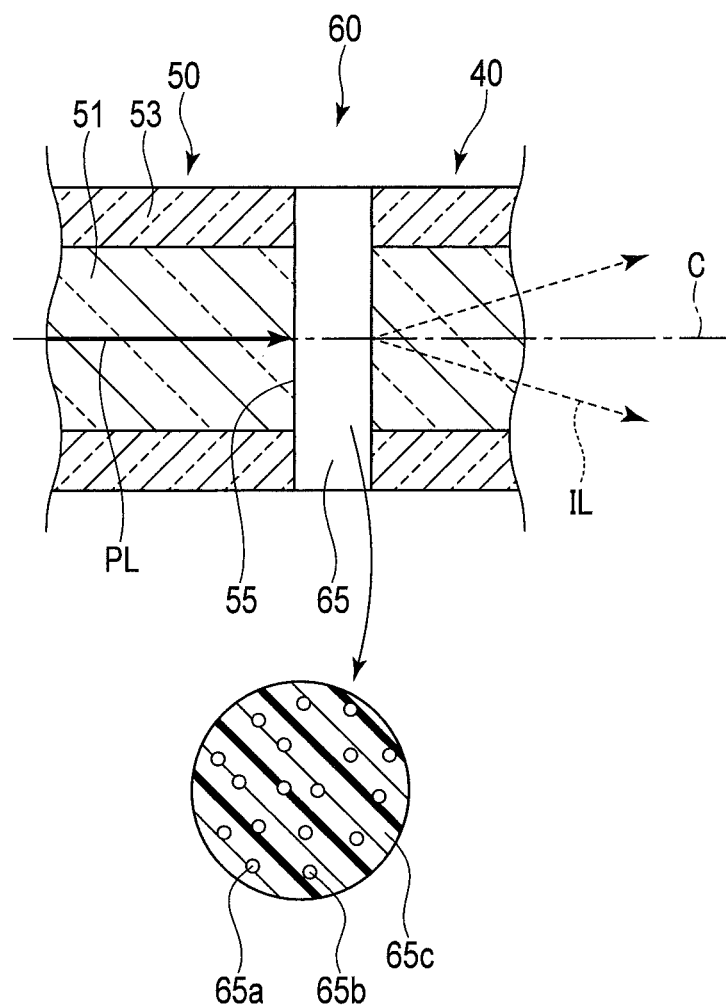
F I G. 14

LIGHTING UNIT

CROSS-REFERENCE TO RELATED APPLICATION

This application is a Continuation Application of PCT Application No. PCT/JP2016/065739, filed May 27, 2016, the entire contents of which are incorporated herein by reference.

BACKGROUND OF THE INVENTION

1. Field of the Invention

The present invention relates generally to a lighting unit having a single core optical fiber.

2. Description of the Related Art

Jpn. Pat. Appln. KOKAI Publication No. 2011-248022, for example, discloses a lighting system having a single core optical fiber. This lighting system adopts, as a light converter, an elliptical diffuser arranged on the distal end surface of the optical fiber to realize wide-range illumination using a laser beam guided by the optical fiber, which is primary light, as illumination light. The diffuser is a member that is provided separately from the optical fiber.

BRIEF SUMMARY OF THE INVENTION

According to one aspect of the present invention, there is provided a lighting unit comprising: a single core optical fiber including an incident end and a distal end, and configured to guide primary light, which is a laser light incident on the incident end, to the distal end; a light converter formed inside the optical fiber, and configured to receive the primary light guided by the optical fiber, convert optical properties of at least part of the received primary light and generate secondary light; and an exit end arranged at the distal end of the optical fiber, and configured to emit the secondary light externally as illumination light.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of a lighting apparatus having a lighting unit according to one embodiment.

FIG. 2 is a diagram showing an example of a distal end portion of an optical fiber in which a light converter and an exit end are formed.

FIG. 3 is a diagram showing an example of a light converter formed at the distal end portion of the optical fiber.

FIG. 4A is a diagram showing an example of a diffusion structure of the light converter.

FIG. 12B is a diagram showing an example of the peripheral surface emitting structure.

FIG. 12C is a diagram showing an example of the peripheral surface emitting structure.

FIG. 12D is a diagram showing an example of the peripheral surface emitting structure.

FIG. 13A is a schematic perspective view of an endoscope system having a lighting apparatus.

FIG. 13B is a diagram showing the configuration of the endoscope system shown in FIG. 13A.

FIG. 14 is a diagram showing an example of a light converting member of the light converter.

DETAILED DESCRIPTION OF THE INVENTION

Figure 4B:
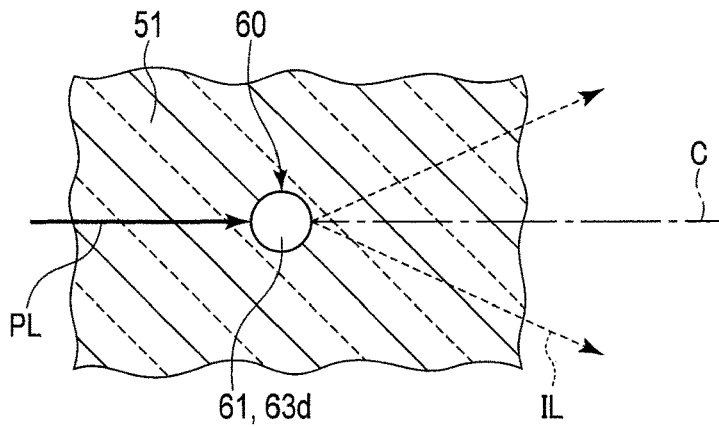
FIG. 4B is a diagram showing an example of the diffusion structure.

Hereinafter, an embodiment of the present invention will be described with reference to the drawings. Some of these drawings may be illustrated by omitting part of the components for clarification of the illustration. The center axis C of a core 51 is regarded as the center axis of an optical fiber 50. The direction of the center axis C indicates a direction, for example, from the incident end 50a to the distal end surface 51c. The central axis of the illumination light IL emitted from the exit end 70 will be referred to as an optical axis. A lighting apparatus 10 shown in FIG. 1 will be explained as an example of an endoscopic lighting apparatus mounted in an endoscope system 110 shown in FIG. 13A. The lighting apparatus 10 may be mounted in a device other than an endoscope, such as a microscope, or may function as an independent device.

As illustrated in FIG. 1, the lighting apparatus 10 includes, for example, a laser light source device 20 for emitting primary light PL, which is a laser beam, and a lighting unit 40 optically connected to the laser light source device 20 for converting the optical properties of at least part of the primary light PL emitted from the laser light source device 20 to generate illumination light IL, and emitting the generated illumination light IL out of the lighting unit 40.

As shown in FIG. 13B, the laser light source device 20 may include laser diodes 22V, 22B, 22G, and 22R. The laser light source device 20 should be configured to emit light with high directivity, and may include LEDs. The detailed configuration of the laser light source device 20 will be described later.

As shown in FIGS. 1 and 2, the lighting unit 40 includes a single core optical fiber 50 as a light guide for guiding the primary light PL emitted from the laser light source device 20, and a light converter 60 that is formed inside the optical fiber 50, receives at least part of the primary light PL guided by the optical fiber 50, converts the optical properties of the at least part of the received primary light PL, and thereby generates secondary light. Furthermore, the lighting unit 40 has an exit end 70 that functions as a distal end portion of the optical fiber 50 on the opposite side with respect to the laser light source device 20, and emits the secondary light to the outside of the optical fiber 50 as illumination light IL. In other words, the optical fiber 50 has the light converter 60 and the exit end 70 and is formed as one body together with the light converter 60 and the exit end 70. That is, the light converter 60 and the exit end 70 are part of the optical fiber 50. According to the present embodiment, the secondary light is emitted to the outside without its optical properties being converted. The light converter 60 therefore generates secondary light as the illumination light IL, by converting the optical properties of the primary light PL.

For the optical fiber 50, a quartz multimode fiber may be adopted. Since the laser light is used as the primary light PL, a single core optical fiber should be adopted for the optical fiber 50 instead of a fiber bundle. The optical fiber 50 is an elongated member that is bendable under an external force. The optical fiber 50 has an incident end 50a that is optically connected to the laser light source device 20 and receives the primary light PL emitted from the laser light source device 20, and an exit end 70 that is disposed on the opposite side with respect to the incident end 50a and emits the illumination light IL. The incident end 50a may be connected directly or indirectly to the laser light source device 20. The optical fiber 50 guides the primary light PL from the incident end 50a to the exit end 70. As shown in FIG. 2, the optical fiber 50 has a core 51 for guiding the primary light PL and the light obtained by converting the optical properties of the primary light PL (e.g., the secondary light or illumination light IL), and a cladding 53 arranged on the periphery the core 51. The cladding 53 has a refractive index lower than the refractive index of the core 51. The cladding 53 has a function of confining in the core 51 the primary light PL and the light obtained by converting the optical properties of the primary light PL (e.g., the secondary light or illumination light IL), using the difference between the refractive index of the core 51 and the refractive index of the cladding 53. The distal end surface 51c of the core 51 and the distal end surface 53c of the cladding 53 may be arranged on the same plane and form a flat surface orthogonal to the center axis C of the core 51. The optical fiber 50 may have a jacket (not shown) to be arranged on the periphery of the cladding 53. The jacket improves the mechanical strength of the optical fiber 50 such as tensile robustness and bending robustness. A resin, such as nylon, acrylic, polyimide, and ETFE, may be used for the jacket.

According to the present embodiment, the light converter 60 is formed inside the core 51, as shown in FIG. 2. Alternatively, as shown in FIG. 3, the light converter 60 may be formed inside the core 51 and the cladding 53. That is, at least part of the light converter 60 should be formed on the center axis C of the core 51. The light converter 60 generates the secondary light that is to be emitted at a light distribution angle larger than or equal to the NA of the optical fiber 50.

In order to generate the secondary light, the light converter 60 has at least one diffusing structure 61 configured to diffuse at least part of the primary light PL traveling inside the core 51, as shown in FIG. 2. It is assumed here that one diffusing structure 61 is adopted.

When the primary light PL having a very narrow light distribution is incident on the diffusing structure 61, the primary light PL is diffused by the diffusing structure 61, as a result of which a diffused light that is illumination light IL having a wide light distribution is generated. In order to diffuse the primary light PL, there must be a difference in refractive index at the interface between the diffusing structure 61 and the core 51 that is an adjacent member with which the diffusing structure 61 is in close contact. The diffusing structure 61 therefore has a refractive index that is different from the refractive index of the core 51. The size of the diffusing structure 61 is approximately the same as, or smaller than, the wavelength of the primary light PL. Specifically, the size of the diffusing structure 61 may be several tens of micrometers or less.

Figure 4C:
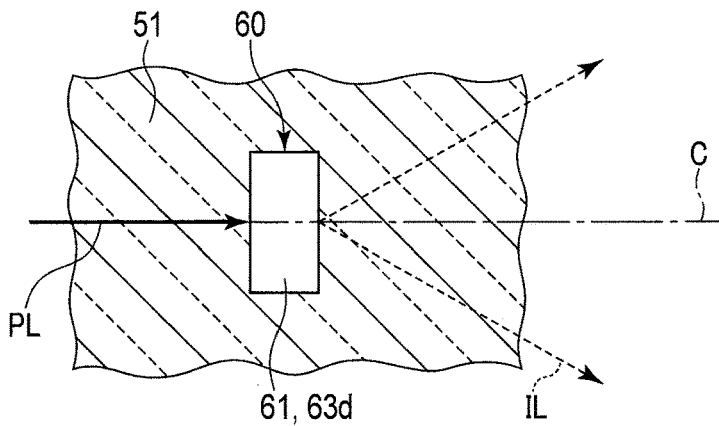
FIG. 4C is a diagram showing an example of the diffusion structure.
Figure 4D:
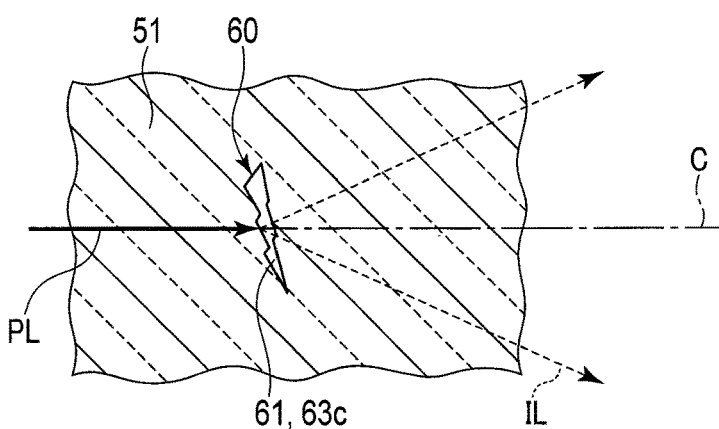
FIG. 4D is a diagram showing an example of the diffusion structure.

The diffusing structure 61 may have various portions or shapes for the diffusion. As illustrated in FIG. 2, the diffusing structure 61 may have a hole 63a. As illustrated in FIG. 4A, the diffusing structure 61 may have a refractive index modified portion 63b having a refractive index higher than the refractive index of the adjacent member. The diffusing structure 61 may have an approximately spherical shape (see FIG. 4B) or an approximately columnar shape (see FIGS. 3 and 4C), or may include a cracked portion 63c (see FIG. 4D). Such a diffusing structure 61 may be formed by laser processing.

If the laser processing is performed on only part of the inside of the core 51, this part evaporates, leaving a hole 63a like a pore (see FIG. 2). The hole 63a is a space filled with a gas, or a vacuum space. The shape and size of the hole 63a are adjusted in accordance with the focused spot diameter, energy density, and irradiating duration of the laser beam that is used for the laser processing. If the diffusing structure 61 has a hole 63a, the diffusing structure 61 may be arranged in the core 51 and the cladding 53, and may be arranged in the radial direction of the optical fiber 50 and in a collinear manner in the core 51 and the cladding 53 of the optical fiber 50, as shown in FIG. 3.

If the laser processing is performed on only part of the inside of the core 51, this part will be reformed so that the refractive index thereof becomes higher than the refractive index of the rest of the core 51 where the laser processing is not performed. The refractive index modified portion 63b shown in FIG. 4A is part of the core 51 reformed by the laser processing. The shape of the refractive index modified portion 63b is not particularly limited. The refractive index can be adjusted according to the focused spot diameter, the energy density, and the irradiating duration of the laser light used for the laser processing. If the diffusing structure 61 has a refractive index modified portion 63b, the diffusing structure 61 may be arranged in the core 51 and the cladding 53, and may be arranged in the radial direction of the optical fiber 50 and in a collinear manner in the core 51 and the cladding 53, as shown in FIG. 3.

When the laser processing is performed on only part of the inside of the core 51, this part may change to an approximately spherical shape (see FIG. 4B) or an approximately columnar shape (see FIG. 4C) by the laser processing. The portion that has changed in shape functions as a diffusing structure 61 having an approximately spherical shape or an approximately columnar shape. The diffusing structure 61 of this type is a space portion 63d covered by the core 51 and formed inside the core 51. When the diffusing structure 61 has an approximately columnar shape (for example, an approximately cylindrical shape), the diffusing structure 61 may penetrate the core 51 in the radial direction of the core 51, as shown in FIG. 3. Furthermore, as shown in FIG. 3, the diffusing structure 61 may be arranged in the core 51 and the cladding 53, and may be arranged in the radial direction of the optical fiber 50 and in a collinear manner in the core 51 and the cladding 53. The diffusing structure 61 of this type may penetrate the core 51 and may be arranged inside the cladding 53. Furthermore, the diffusing structure 61 may penetrate the core 51 and the cladding 53 in a collinear manner, as shown in FIG. 3. The shape and size of the diffusing structure 61 can be adjusted in accordance with the focused spot diameter, energy density, and irradiating duration of the laser light that is used for the laser processing. When the diffusing structure 61 has an approximately columnar shape (for example, approximately cylindrical shape), the central axis of the diffusing structure 61 does not have to be orthogonal to the center axis C.

When the laser processing is performed on only part of the core 51, a crack may be generated in this part by the laser processing. The cracked portion functions as a cracked portion 63c (see FIG. 4D). The size and shape of the cracked portion 63c can be adjusted in accordance with the focused spot diameter, energy density, and irradiating duration of the laser light that is used for the laser processing.

The refractive index of the diffusing structure 61 in the hole 63a, the approximately spherical or columnar shape, and the cracked portion 63c can be adjusted in accordance with the focusing spot diameter, the energy density, and the irradiating duration of the laser light that is used for the laser processing. As a result of this laser processing, the diffusing structure 61 is formed with its refractive index different from the refractive index of the core 51 and with its size adjusted.

Figure 5:
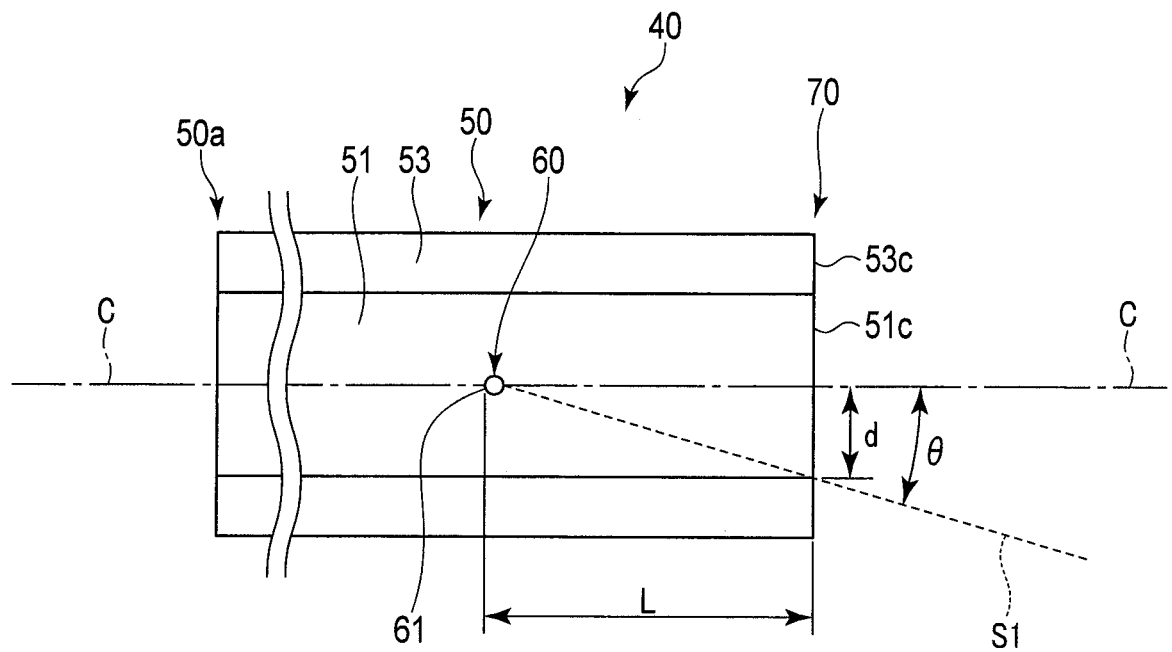
FIG. 5 is a diagram explaining the position of the diffusion structure in a cross section including the central axis of the core of the optical fiber.

Next, the arrangement of the light converter 60 (diffusing structure 61) in the direction of the center axis C of the core 51 will be described with reference to FIG. 5.

In a multimode optical fiber 50, the light distribution angle of the guided light can be widened further than a single mode optical fiber 50. Therefore, even without using the diffusing structure 61, illumination light having a wide light distribution angle defined by the NA unique to the optical fiber 50 may be emitted. According to the present embodiment, however, by adopting the diffusing structure 61, an illumination light IL with a still wider light distribution angle can be emitted. The light distribution angle of the illumination light IL therefore becomes wider than the NA of the optical fiber 50.

If the light distribution angle of the illumination light IL is wider than the NA of the optical fiber 50, the illumination light IL cannot be confined in the core 51 at the interface between the core 51 and the cladding 53. That is, part of the illumination light IL may leak out of the optical fiber 50 through the cladding 53 of the optical fiber 50 before reaching the exit end 70. For the illumination light IL to reach the exit end 70 without leaking through the cladding 53, the distance between the light converter 60 (diffusing structure 61) and the exit end 70 in the direction of the center axis C of the core 51 plays a key role.

Here, the exit end 70 is defined as the distal end surface 51c of the core 51. The radius of the core 51 is referred to as d, the angle at which the optical fiber 50 can accept the secondary light is referred to as NA, the refractive index of the external space of the optical fiber 50 is referred to as n, and the angle formed between a line S1 and the center axis C of the core 51 is referred to as θ. The line S1 is a line segment connecting the diffusing structure 61 arranged on the center axis C of the core 51 and the edge of the distal end surface 51c. The distance between the light converter 60 (diffusing structure 61) and the exit end 70 (distal end surface 51c) in the direction of the center axis C of the core 51 is referred to as L. Here, the following expressions (1) and (2) are established by d, NA, n, θ, and L.

$$NA = n \times \sin\theta \quad (1)$$

$$L \leq d/\tan\theta \quad (2)$$

L satisfies the following expression (3) by removing θ from the expressions (1) and (2).

$$L \leq \frac{d \times n \times \sqrt{1 - \left(\frac{NA}{n}\right)^2}}{NA} \quad (3)$$

According to the present embodiment, the diffusing structure 61 is arranged on the center axis C of the core 51 so as to satisfy the expression (3). Thus, the illumination light IL having a light distribution angle larger than the NA of the optical fiber 50 reaches the exit end 70 without leaking to the outside through the cladding 53, and is externally emitted only through the exit end 70 (distal end surface 51c).

As shown in FIG. 13B, the light converters 60 arranged at such a position are positioned inside the distal end portion of the insertion portion 121 (see FIG. 13B) of the endoscope 120 and away from the laser light source device 20.

Figure 6:
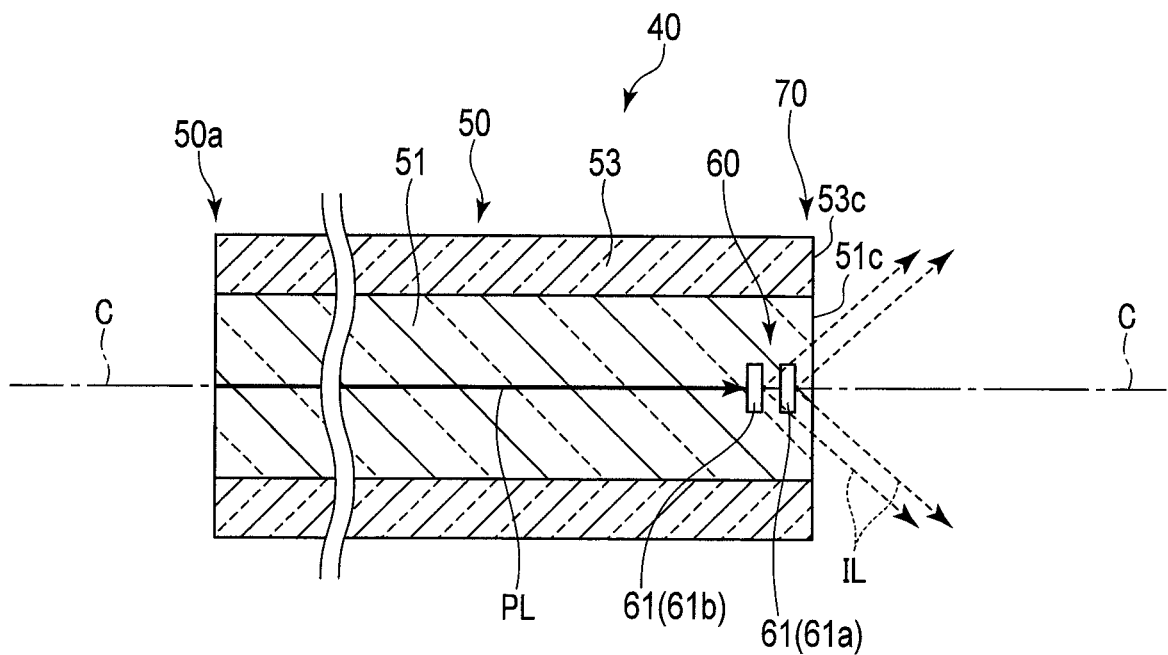
FIG. 6 is a diagram showing an example of the arrangement of a plurality of diffusion structures in the cross section including the central axis of the core of the optical fiber.

As long as the expression (3) is satisfied, a plurality of diffusing structures 61 may be arranged in the direction of the center axis C of the core 51, as illustrated in FIG. 6. As long as the expression (3) is satisfied, the arrangement position of the diffusing structures 61 does not have to be particularly limited. The number of diffusing structures 61 may be adjusted as needed, such as several to several hundred or several thousand, in accordance with the size of each diffusing structure 61 or the thickness of the optical fiber 50. Depending on the number of diffusing structures 61, the distribution of the illumination light IL is adjusted. For example, when a plurality of diffusing structures 61 are arranged on the center axis C of the core 51, the primary light PL is diffused in each of the diffusing structures 61, which means that the diffusion is performed a plurality of times. As a result, the illumination light IL having a larger light distribution angle can be provided, and the intensity distribution of the illumination light IL can be adjusted at the exit end 70 (the distal end surface 51c of the core 51).

When a plurality of diffusing structures 61 are provided, the density of the diffusing structures 61 may be determined to be the same, or to be different from each other. For example, the density of the first diffusing structure 61a arranged near the exit end 70 (distal end surface 51c) with respect to the direction of the center axis C of the core 51 may be higher than the density of the second diffusing structure 61b that is positioned away from the exit end 70 (distal end surface 51c). Alternatively, the density of the first diffusing structure 61a may be lower than the density of the second diffusing structure 61b with respect to the direction of the center axis C of the core 51. The density here represents the degree of diffusion, where the effect of widening the light distribution is larger with a higher density, while the effect of widening the light distribution is smaller with a lower density. The density may be adjusted by the size of the diffusing structure 61, the shape of the diffusing structure 61, and the focused spot diameter, energy density, and irradiating duration of the laser light used for the laser processing. The number of diffusing structures 61 having different densities is not particularly limited.

The plurality of diffusing structures 61 can diffuse the primary light in stages, or in other words, at the respective diffusing structures 61 in the direction of the center axis C, and the level of diffusion can be adjusted at the respective diffusing structures 61. As a result, the light distribution of a desired width can be realized. Here, one diffusing structure 61 and a plurality of diffusing structures 61 that are designed to realize the light distribution of the same width are compared. In comparison with one diffusing structure 61, the plurality of diffusing structures 61 can be designed to provide the effects of dispersing the heat locally generated in accordance with the diffusion and reducing the loss of the illumination light IL due to the generation of the backward illumination light BIL, which will be described later.

As shown in FIG. 6, when a plurality of diffusing structures 61 are arranged in the direction of the center axis C, the second diffusing structure 61b diffuses part of the primary light PL to generate the secondary light, which is the diffused light. Part of the secondary light is emitted to the outside of the optical fiber 50 as the illumination light IL, without its optical properties being converted. The second diffusing structure 61b therefore generates this secondary light as illumination light IL. The remaining part of the secondary light is incident on the first diffusing structure 61a. The first diffusing structure 61a transforms the optical properties of this part of the secondary light, which means that it diffuses the secondary light. The diffused secondary light is emitted as illumination light IL to the outside of the optical fiber 50, without its optical properties being converted. The first diffusing structure 61a therefore generates the diffused secondary light as illumination light IL. In this manner, when a plurality of diffusing structures 61 are arranged in the direction of the center axis C, the light converter 60 generates, as the illumination light IL, the light obtained by converting the optical properties of the primary light PL.

Next, an example of the arrangement of the light converter 60 (diffusing structures 61) in the cross section perpendicular to the center axis C of the core 51 will be described, with reference to FIG. 7. The perpendicular cross section denotes a plane in the radial direction of the core 51.

In the perpendicular cross section, the distribution of the primary light PL in the optical fiber 50 may depend on the records of incidence such as the light amount of the primary light PL incident on the optical fiber 50, and the shape of the entire optical fiber 50 such as being bent or linearly extending. For this reason, although the distribution cannot be generalized, the intensity of the primary light PL tends to be higher on the center axis C of the core 51 and lower further away from the center axis C of the core 51 in the perpendicular cross section. In other words, the intensity at the central portion of the primary light PL is high, while the intensity at the peripheral portion of the central portion of the primary light PL is low. Thus, in order to obtain the illumination light IL having a uniform intensity and a symmetrical light distribution at the exit end 70 (distal end surface 51c of the core 51), the diffusing structure 61 should diffuse more at the center of the primary light PL than the peripheral portion of the primary light PL.

For example, a plurality of diffusing structures 61 may be arranged in the cross section perpendicular to the center axis C of the core 51. A third diffusing structure 61c and a fourth diffusing structure 61d having a lower density than the third diffusing structure 61c are arranged in the perpendicular cross section. In consideration of the emission of the illumination light IL having a uniform intensity and the intensity of the primary light PL, the third diffusing structure 61c is arranged on the center axis C of the core 51, while the fourth diffusing structure 61d is arranged in the periphery of the center axis C of the core 51. The fourth diffusing structure 61d may be arranged in a ring shape around the center axis C and around the periphery of the third diffusing structure 61c. The third diffusing structure 61c is therefore arranged inside the ring. A fifth diffusing structure (not shown) having a density lower than the fourth diffusing structure 61d may be arranged around the fourth diffusing structure 61d. That is, the number of diffusing structures 61 having different densities is not particularly limited, and the diffusing structures 61 may be concentrically arranged around the center axis C of the core 51. In this manner, the illumination light IL with a uniform intensity and a symmetrical light distribution at the exit end 70 (the distal end surface 51c of the core 51) can be obtained. Furthermore, the primary light PL, which has a narrow light distribution and is guided by the multimode optical fiber 50, is distributed mainly in the center portion of the core 51. By arranging a high-density diffusing structure 61 in the central portion, the primary light PL having a narrow light distribution can be effectively diffused. In other words, a high-density diffusing structure 61 arranged in the central portion would not overly diffuse the primary light PL that is propagating through the optical fiber 50 with an already relatively wide light distribution, but would mainly diffuse the primary light PL with a narrow light distribution. This diffusing structures 61 therefore offer the effects of reducing the heat generation accompanying the diffusion and reducing the loss of the illumination light IL due to the diffusion.

Figure 7:
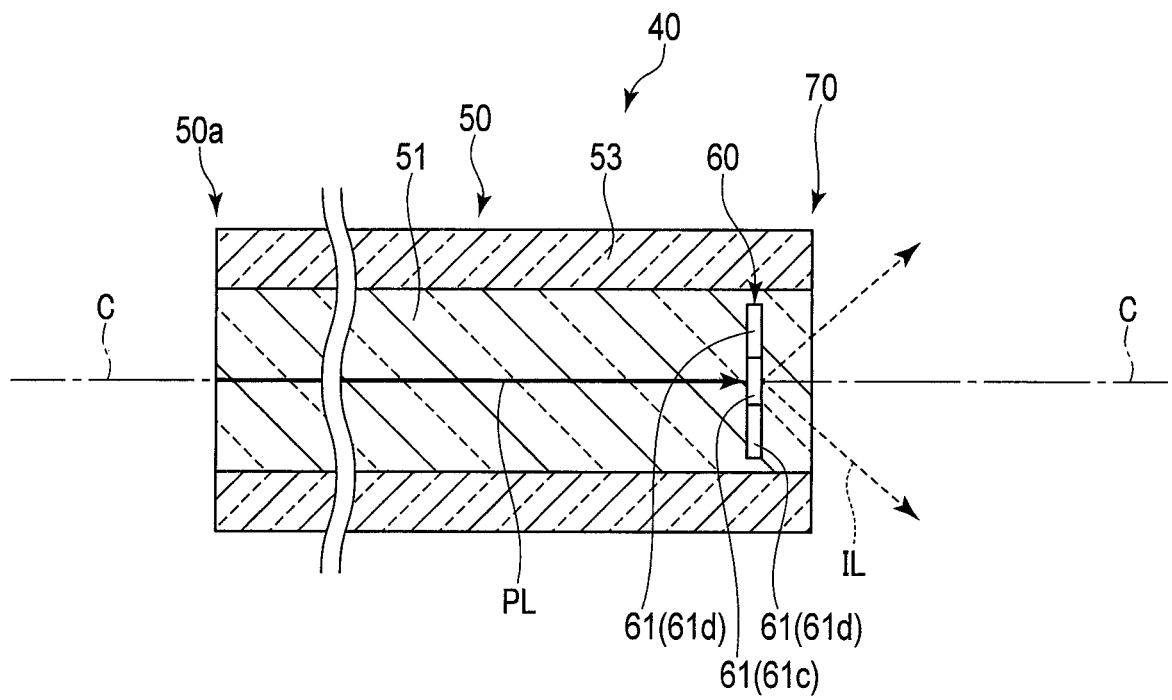
FIG. 7 is a diagram for explaining an example of the arrangement of the diffusion structures in the cross section including the central axis of the core of the optical fiber.

As shown in FIG. 7, when a plurality of diffusing structures 61 are arranged in a cross section perpendicular to the center axis C, the diffusing structures 61c and 61d diffuse part of the primary light PL and generate the secondary light. The secondary light is emitted to the outside of the optical fiber 50 without its optical properties being converted. The diffusing structures 61c and 61d therefore generate the secondary light as the illumination light IL. As discussed above, when a plurality of diffusing structures 61 are arranged in a cross section perpendicular to the center axis C, the light converter 60 generates the secondary light as the illumination light IL by converting the optical properties of the primary light PL.

Figure 8A:
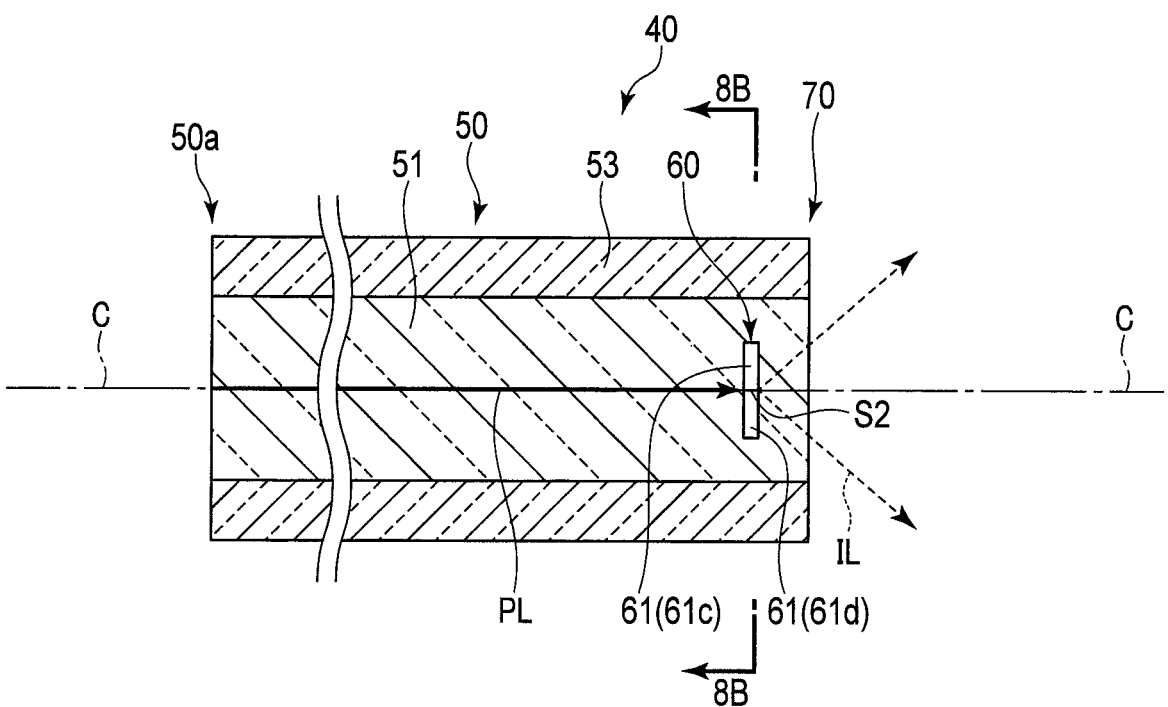
FIG. 8A is a diagram showing an example of the arrangement of a plurality of diffusion structures in the cross section including the central axis of the core of the optical fiber.
Figure 8B:
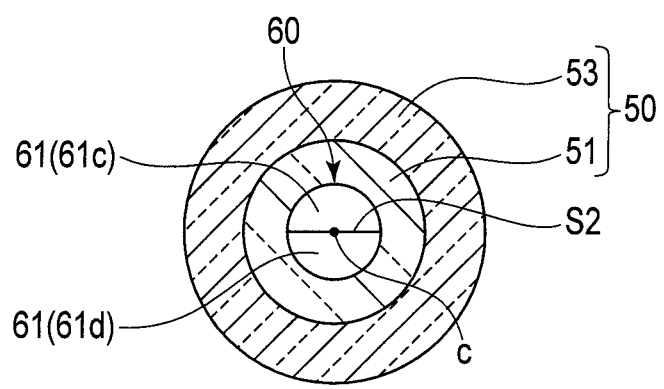
FIG. 8B is a cross-sectional view, taken along the line 8B-8B shown in FIG. 8A.
Figure 8C:
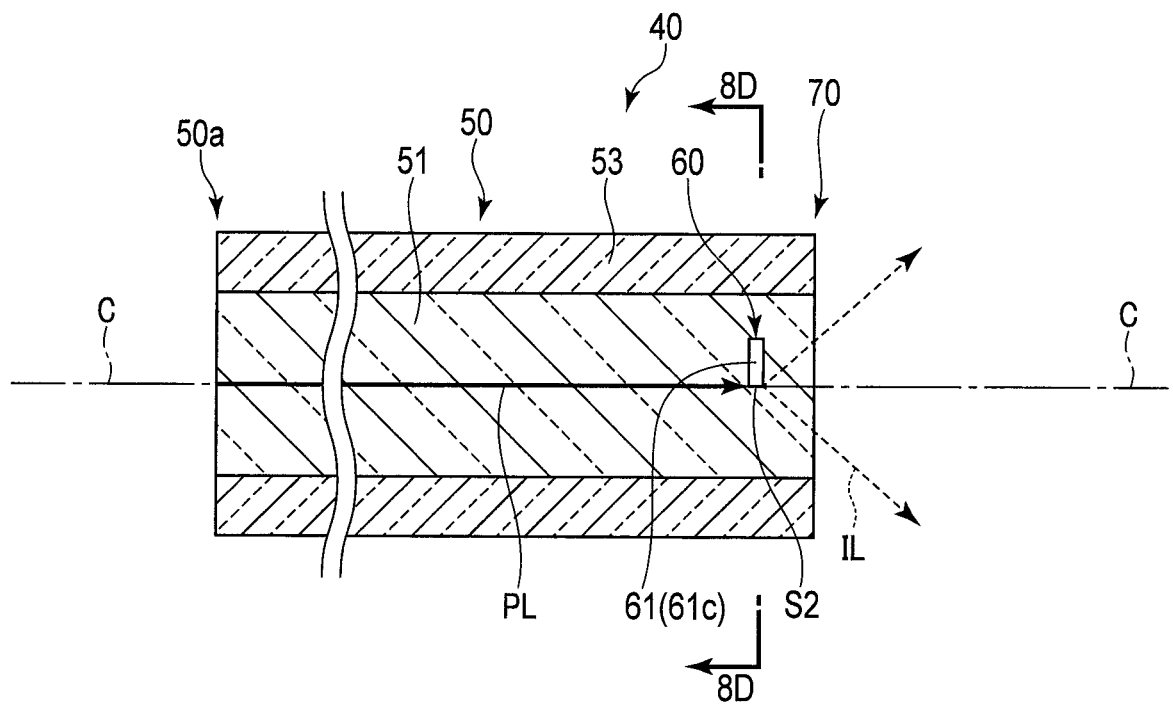
FIG. 8C is a diagram showing an example of the arrangement of the diffusion structure in the cross section including the central axis of the core of the optical fiber.
Figure 8D:
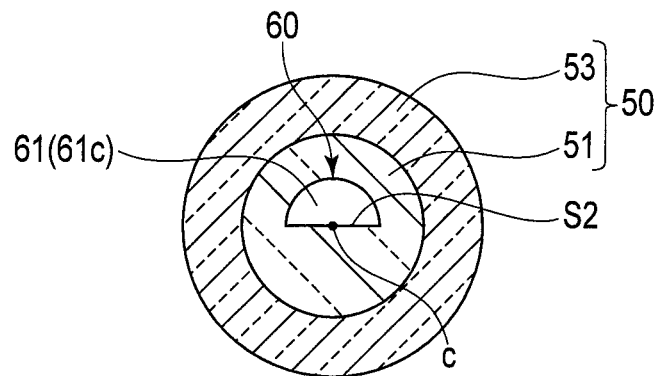
FIG. 8D is a cross-sectional view, taken along the line 8D-8D shown in FIG. 8C.

For example, when the lighting apparatus 10 is mounted on the endoscope system 110, the exit end 70 is arranged at the distal end of the insertion portion 121 of the endoscope 120 together with an imaging device (not shown) such as a CMOS. There may be circumstances in which, in accordance with the positional relationship between the exit end 70 and the imaging device and the light receiving sensitivity of the imaging device, the intensity of the illumination light IL is preferably uneven and the distribution of the illumination light IL is preferably asymmetric with respect to the center axis C of the core 51. If this is the case, as shown in FIGS. 8A and 8B, the third diffusing structure 61c and the fourth diffusing structure 61d may be arranged with the longitudinal cross section S2 interposed in between, where the longitudinal cross section S2 is a cross section including the center axis C of the core 51. That is, the third diffusing structure 61c may be arranged on the front side of the longitudinal cross section S2, while the fourth diffusing structure 61d may be arranged on the back side of the longitudinal cross section S2. The term "front side" here refers to one of the two halves divided by the longitudinal cross section S2, whereas the "back side" refers to the other one of the two halves. In other words, when one of the two halves is determined as the front side, the other one is the back side. The third diffusing structure 61c and the fourth diffusing structure 61d may be arranged symmetrically with respect to the longitudinal cross section S2. Alternatively, as shown in FIGS. 8C and 8D, one diffusing structure 61 (e.g., the third diffusing structure 61c) may be arranged on the front side, which is one half of the longitudinal cross section S2. In this manner, the illumination light IL having an uneven intensity and being asymmetrical with respect to the center axis C of the core 51 can be obtained. The number and shape of diffusing structures 61 having different densities are not particularly limited.

Figure 9A:
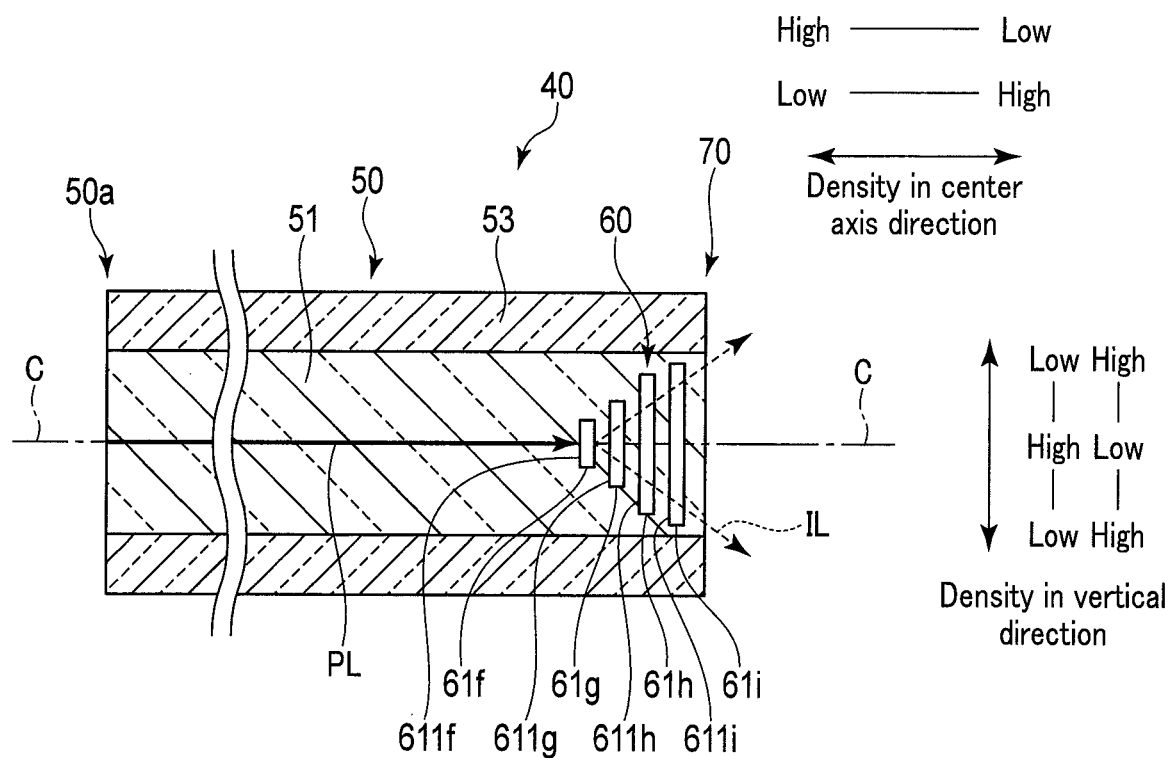
FIG. 9A is a diagram explaining a combination of the arrangement of a plurality of diffusion structures in the central axis direction, and the arrangement of a plurality of diffusion structures in the vertical direction in the cross section including the central axis of the core of the optical fiber.

As shown in FIG. 9A, the arrangement of the diffusing structures 61 in the direction of the center axis C of the core 51 may be combined with the arrangement of the diffusing structures 61 in the perpendicular direction.

As shown in FIG. 9A, the density of the diffusing structures 61 may increase or decrease from the laser light source device 20 to the exit end 70 in the direction of the center axis C of the core 51. The density of the diffusing structures 61 may increase or decrease from the center axis C of the core 51 toward the cladding 53 in the perpendicular direction. Furthermore, a sixth, seventh, eighth, and ninth diffusing structures 61f, 61g, 61h, and 61i may be arranged from the laser light source device 20 to the exit end 70, and include a sixth, seventh, eighth, and ninth irradiation regions 611f, 611g, 611h, and 611i, respectively, onto which the primary light PL is incident. The irradiation area becomes larger in the increasing order of the sixth, seventh, eighth, and ninth irradiation regions 611f, 611g, 611h, and 611i. Alternatively, the irradiation region may become smaller in the order of the sixth, seventh, eighth, and ninth irradiation regions 611f, 611g, 611h, and 611i.

Figure 9B:
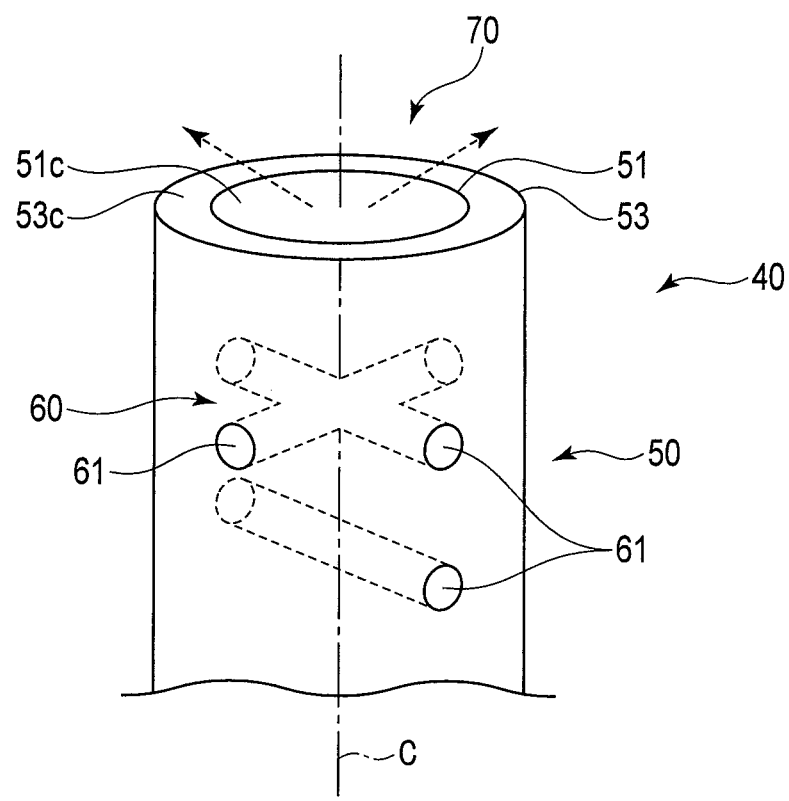
FIG. 9B is a diagram showing an example of the combination shown in FIG. 9A.

A plurality of diffusing structures 61 may be arranged, with each of the diffusing structures 61 having an approximately columnar shape (e.g., approximately cylindrical shape), as shown in FIG. 9B. The central axes of the diffusing structures 61 do not have to be parallel to each other. One diffusing structure 61 may intersect with another diffusing structure 61.

Figure 10:
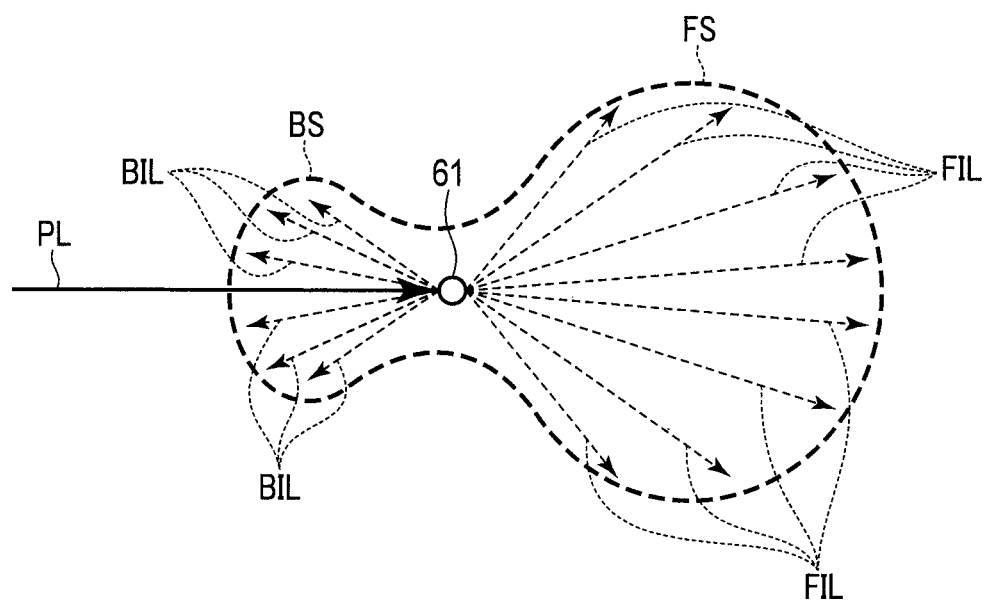
FIG. 10 is a diagram explaining Mie scattering.

Next, the diffusing phenomenon will be described with reference to FIG. 10. In FIG. 10, the behavior of the primary light PL at the time of the primary light PL being incident on one diffusing structure 61 is illustrated for the simplicity of explanation.

The diffusing phenomenon may be divided mainly into Mie scattering as shown in FIG. 10 and Rayleigh scattering that is not shown.

Mie scattering shown in FIG. 10 occurs when the diameter of the diffusing structure 61 is approximately the same as the wavelength of the primary light PL. Mie scattering provides more forward diffusion components FS, which are the components of the primary light PL scattering forward, and fewer backward diffusion components BS, which are the components of the primary light PL scattering backward.

Rayleigh scattering (not shown) occurs when the diameter of the diffusing structure 61 is approximately one tenth of the wavelength of the primary light PL or smaller. Rayleigh scattering provides forward diffusion components FS and backward diffusion components BS approximately in equal amounts.

In consideration of the brightness of the forward illumination light FIL emitted forward from the exit end 70, it is preferable to adopt Mie scattering that provides more forward diffusion components FS than backward diffusion components BS. On the other hand, if multicolor primary light PL is to be scattered, the wavelength dependency of the scattering should be taken into consideration. In general, Mie scattering is considered to be more wavelength-dependent than Rayleigh scattering, and therefore Rayleigh scattering is more preferable in order to reduce the color unevenness of the forward illumination light FIL.

As described above, the diameter of the diffusing structure 61 may be determined in accordance with the usage. In the present embodiment, Mie scattering is adopted for the lighting apparatus 10. This means that the diameter of the diffusing structure 61 is approximately one tenth of the wavelength of the primary light PL or larger. In particular, if the primary light PL used as the illumination light IL has a wavelength of, for example, approximately 400 to 800 nm, the diameter of the diffusing structure 61 will be 40 nm or more.

In the above description, the diffusing phenomenon of a single diffusing structure 61 has been discussed. In the lighting unit 40 according to the present embodiment, one or more diffusing structures 61 may be included in the optical fiber 50. The diffusing phenomenon of the lighting unit 40 for any case is basically similar to the diffusing phenomenon of a single diffusing structure 61.

Whether Mie scattering or Rayleigh scattering is adopted, not only forward diffusion components FS but also backward diffusion components BS will be generated at the time of generating the illumination light IL. The forward diffusion components FS are used as forward illumination light FIL, but the backward diffusion components BS do not contribute to the forward illumination light FIL. It is assumed here that the optical fiber 50 is arranged inside the endoscope 120. In such an arrangement, part of the backward diffusion components BS may leak from the optical fiber 50 to the surrounding members arranged around the optical fiber 50 as backward illumination light BIL and may be absorbed by the surrounding members. The surrounding members may include the exterior of the insertion portion 121. The absorbed backward illumination light BIL is converted into heat, by which the surrounding members may cause heat and increase their temperature. As a result, the tract (e.g., the intestinal tract of the patient, not shown) into which the insertion portion 121 is inserted may be damaged by the heat when the insertion portion 121 comes into contact with the inner wall of the tract.

According to the present embodiment, however, most of the backward illumination light BIL is reversed in the optical fiber 50 in the state of being confined in the core 51 by the diffusing structure 61 to reach the laser light source device 20. Thereafter, the backward illumination light BIL is released outside as heat from the laser light source device 20 that is arranged at a position away from the diffusing structure 61. Because the backward illumination light BIL will not be absorbed by the surrounding members, the increase in the temperature of the insertion portion 121 can be controlled. That is, even when the insertion portion 121 is inserted into, for example, a tract and comes into direct contact with the inner wall of the tract, the possibility of the tract being damaged by heat can be eliminated. As described above, the temperature rise of the surrounding members can be suppressed, and the heat is released from the laser light source device 20 arranged at a position away from the distal end portion of the insertion portion 121 according to the present embodiment. In this manner, the influence of the heat on the tract can be reduced. Furthermore, when the diffusing structure 61 diffuses the primary light PL, or in other words, when the illumination light IL is generated, the heat generated from the light converter 60 can be minimized.

The diffusing structure 61 is formed in the post-processing of the ordinary optical fiber 50. For example, the diffusing structure 61 may be formed by laser processing using a femtosecond laser. With the laser processing, a three-dimensional structure can be created inside transparent parts such as the core 51 and the cladding 53. By narrowing the spot diameter of the laser light for laser processing, minute components such as the core 51 can be processed to provide a fine shape. In the laser processing, when irradiating the processing-targeted optical fiber 50 with the processing laser light, the focal point of the processing laser light is adjusted by a lens (not shown) or the like so as to be positioned inside the optical fiber 50, for example in the core 51. A diffusing structure 61 is formed at this focal point. The detailed discussion regarding the principle of the laser processing will be omitted. However, the laser processing is such that only the focal point portion where the energy density of the processing laser light reaches or exceeds a certain level is processed as the diffusing structure 61, while the periphery of the focal point portion will not be processed. Furthermore, the processing laser light causes small damage to the periphery of the focal point portion. The diffusing structure 61 may be suitably formed as a hole 63a, a refractive index modified portion 63b, an approximately spherical shape, an approximately columnar shape, a cracked portion 63c, and the like, by appropriately adjusting the focused spot diameter, the energy density, and the irradiating duration. For example, the processing laser light is emitted from the outer peripheral surface of the cladding 53 or the distal end surface 51c of the core 51 toward the core 51. When the processing laser light is emitted from the outer peripheral surface of the cladding 53 toward the core 51, the diffusing structure 61 may be formed in the core 51 and the cladding 53 as shown in FIG. 3.

As shown in FIGS. 1 and 2, the distal end surface of the optical fiber 50 has a distal end surface 51c of the core 51 and the distal end surface 53c of the cladding 53, and the exit end 70 may function as at least part of the distal end face of this optical fiber 50. The exit end 70 is arranged in the distal end surface of the optical fiber 50 and has an end surface emitting structure 71 through which the illumination light IL is emitted. For example, the end surface emitting structure 71 provides the illumination light IL of a uniform intensity, and functions so that most of the illumination light IL can be used. The end surface emitting structure 71 may be formed by cutting the distal end surface of the optical fiber 50 in a direction perpendicular to the center axis C of the core 51 and polishing the distal end surface of the optical fiber 50. Irregularities and undulations locally formed by the cutting can be removed from the distal end surface of the optical fiber 50 by polishing. In other words, the end surface emitting structure 71 functions as a flat exit end surface. The illumination light IL is emitted from the distal end surface 51c of the core 51. Thus, the end surface emitting structure 71 should be arranged at least in the distal end surface 51c of the core 51. That is, at least the flat distal end surface 51c of the core 51 should function as the exit end 70 (exit end surface).

Figure 11A:
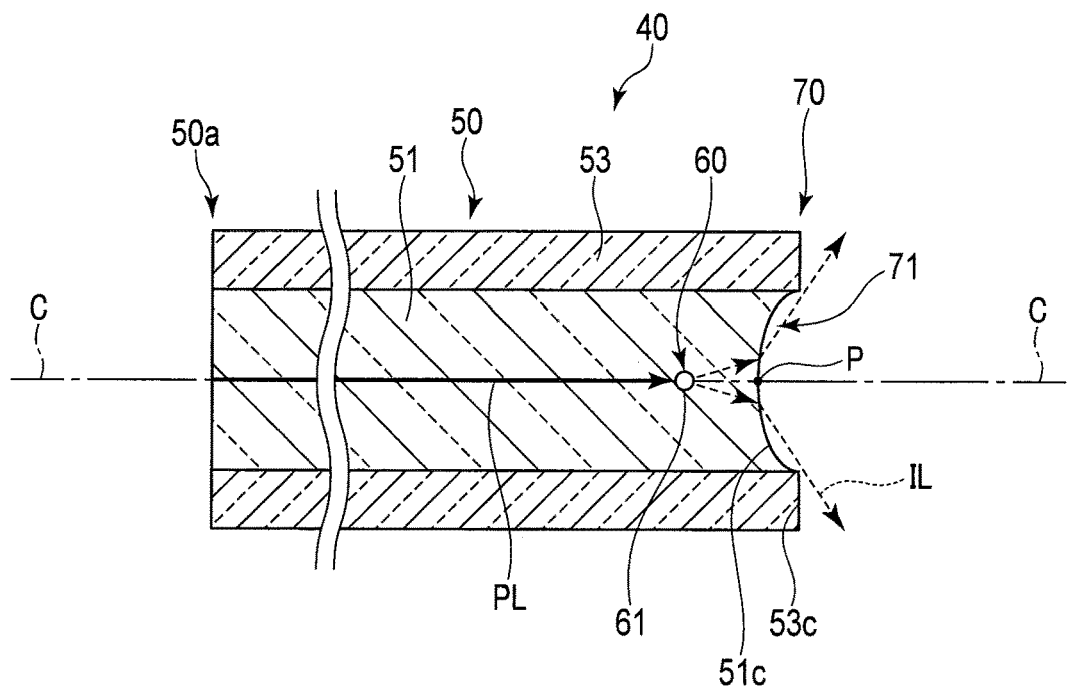
FIG. 11A is a diagram showing an example of an end surface emitting structure of the exit end.
Figure 11B:
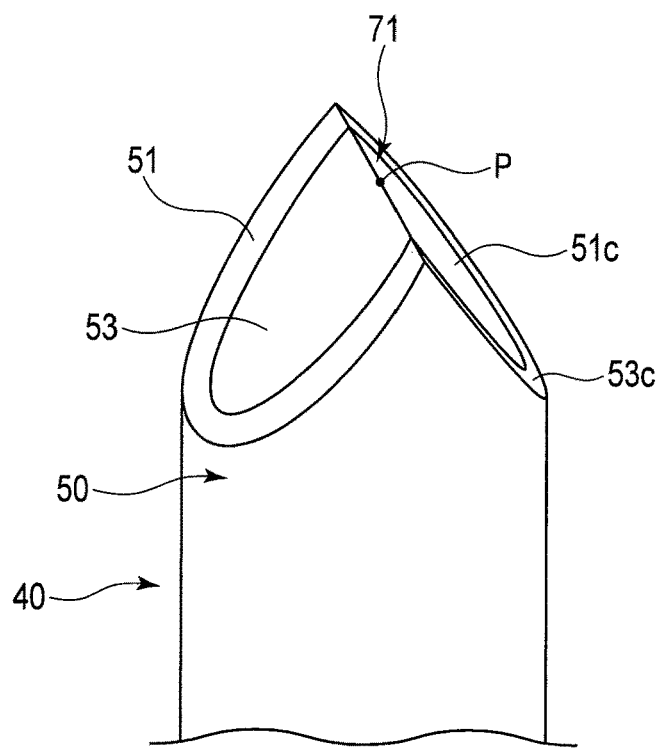
FIG. 11B is a diagram showing an example of the end surface emitting structure.
Figure 11C:
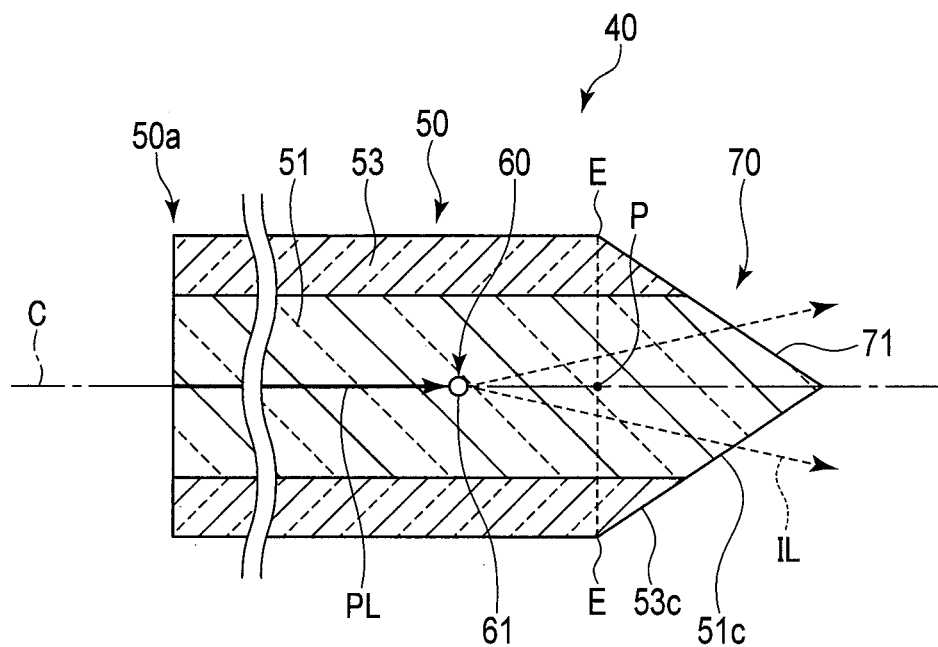
FIG. 11C is a diagram showing an example of the end surface emitting structure.
Figure 11D:
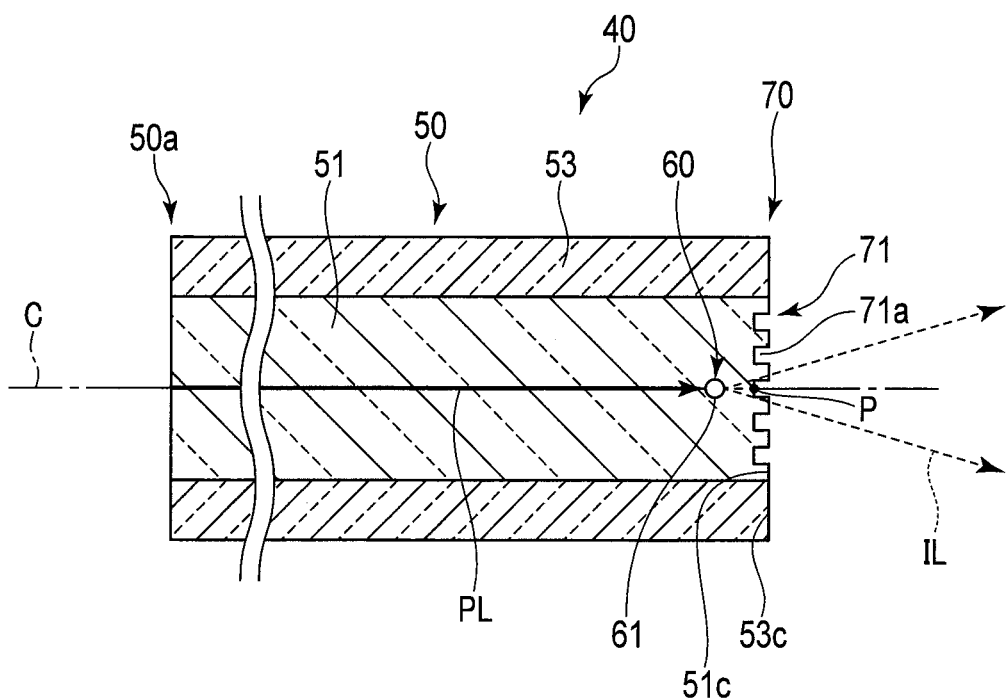
FIG. 11D is a diagram showing an example of the end surface emitting structure.
Figure 11E:
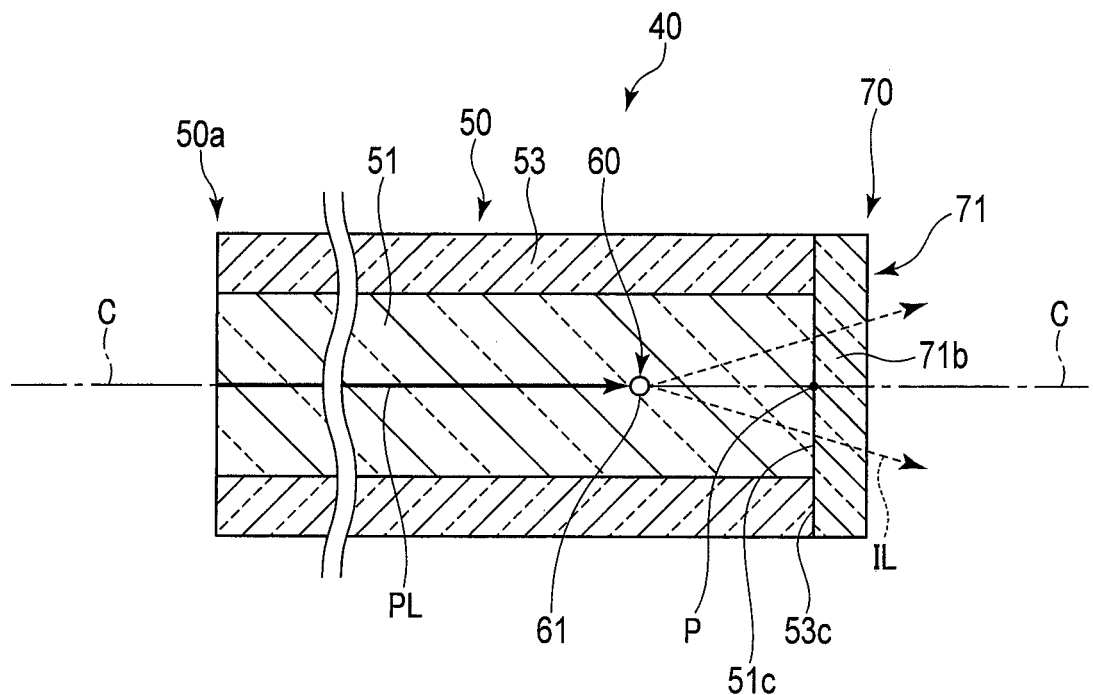
FIG. 11E is a diagram showing an example of the end surface emitting structure.

The end surface emitting structure 71 is not limited to a flat form; it may have at least one of a flat form, a concave lens form that is concaved toward the laser light source device 20 as illustrated in FIG. 11A, a wedge form as illustrated in FIG. 11B, and a tapered pencil form as illustrated in FIG. 11C. If the end surface emitting structure 71 has a lens form as in FIG. 11A, a wide light distribution can be efficiently realized together with the diffusion. The end surface emitting structure 71 may have one of an uneven portion 71a processed in the distal end surface 51c of the core 51 as illustrated in FIG. 11D, and an anti-reflection coat 71b as illustrated in FIG. 11E. The anti-reflection coat 71b may be a single layer coating of magnesium fluoride or the like, or may be a multilayer coating if wide-range wavelength prevention performance or high antireflection performance is required.

Here, the reference position for the distance L (see FIG. 5) on the distal end surface 51c of the core 51 is referred to as a reference position P. For the lens form shown in FIG. 11A and the uneven portion 71a shown in FIG. 11D, the reference position P is located at the bottom of the lens form or the uneven portion 71a. In the wedge form shown in FIG. 11B, the reference position P is located at the tip of the shape. In the pencil form shown in FIG. 11C, the reference position P is at the intersection point of the cross section and the center axis C of the core 51, where the cross section is at the end point E of the tapering processing. The cross section is perpendicular to the center axis C of the core 51, and is a plane that extends in the radial direction of the core 51. The cross section including the end point E is the outer edge of the processing, and is located at the boundary between the cylindrical portion and the tapered portion of the fiber. In FIG. 11E, the reference position P is located on the distal end surface 51c of the core 51. Since the anti-reflection coat 71b is extremely thin, the reference position P may be located on the anti-reflection coat 71b.

The exit end 70 may be the distal end surface of the optical fiber 50 and the outer peripheral surface of the optical fiber 50 between this distal end surface and the light converter 60. The structure of the exit end 70 at the distal end surface is the same as the end surface emitting structure 71, and therefore will be omitted from the explanation.

Figure 12A:
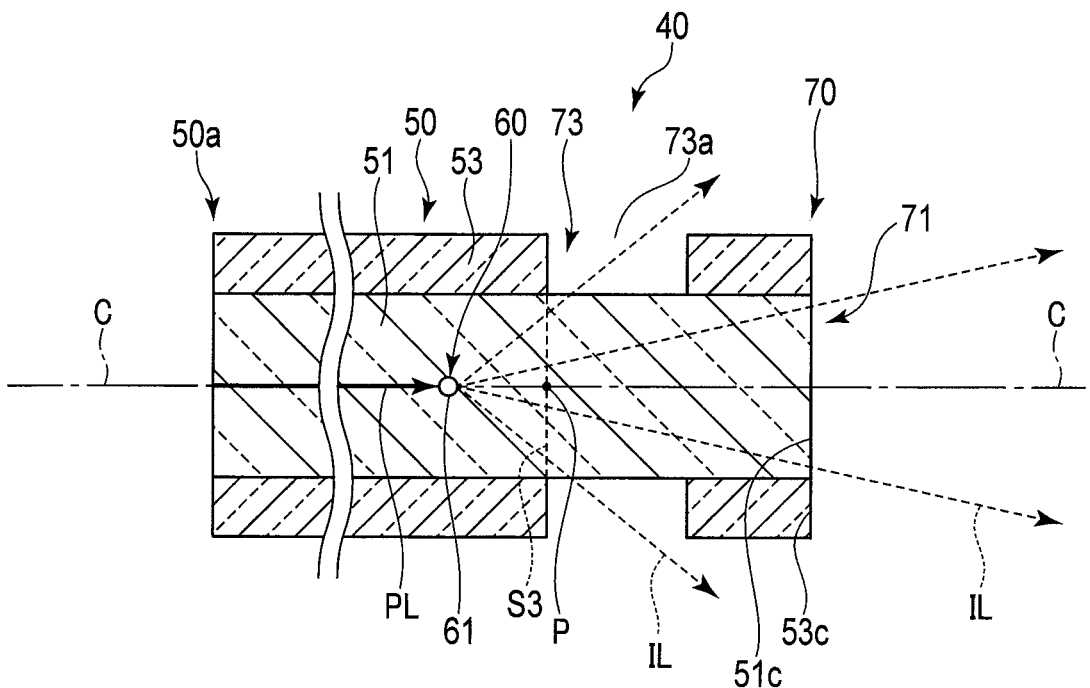
FIG. 12A is a diagram showing an example of a peripheral surface emitting structure of the exit end.

As shown in FIG. 12A, the exit end 70 may include a peripheral surface emitting structure 73 arranged on the outer peripheral surface of the optical fiber 50 between the distal end surface of the optical fiber 50 and the light converter 60 to emit the illumination light IL from the outer peripheral surface of the optical fiber 50. The peripheral surface emitting structure 73 functions, together with the light converter 60, to provide illumination light IL having a wide light distribution. The peripheral surface emitting structure 73 may include a cutout portion 73a formed in the cladding 53 by laser processing so as to expose the outer peripheral surface of the core 51. The cutout portion 73a may be arranged in a ring form around the entire outer peripheral surface of the cladding 53 as illustrated in FIG. 12B, or in a dotted pattern in the outer peripheral surface of the cladding 53 as illustrated in FIG. 12C. In the peripheral surface emitting structure 73, the reference position P is the intersection point of the center axis C of the core 51 and the line S3 connecting the cutout portion 73a and the center axis C of the core 51. The line S3 is a straight line extending from the position closest to the laser light source device 20 to the center axis C in the cutout portion 73a. In the peripheral surface emitting structure 73, the illumination light IL is emitted from the core 51 to the outside through the outer peripheral surface of the core 51 and the cutout portion 73a. As illustrated in FIG. 12D, the peripheral surface emitting structure 73 may function as the outer peripheral surface of the core 51 exposed to the outside by removing the cladding 53. The illumination light IL is emitted from the core 51 to the outside through the outer peripheral surface of the core 51.

The endoscope system 110 including the lighting apparatus 10 will be described with reference to FIGS. 13A and 13B.

The endoscope system 110 as shown in FIG. 13A may be installed in an examination room or an operating room. The endoscope system 110 has an endoscope 120 for taking images of the inside of a tract of a patient such as a lumen, and an image processing device 130 for processing the images of the inside of the tract taken by the imaging unit (not shown) of the endoscope 120. The endoscope system 110 includes a display unit 140 connected to the image processing device 130 for displaying images that have been processed by the image processing device 130, and a light source device 20 for emitting the primary light PL used for emitting the illumination light IL from the endoscope 120.

The endoscope 120 of FIG. 13A may function as an insertion device to be inserted into a tract. The endoscope 120 may be a direct view-type endoscope or a side view-type endoscope.

Although the endoscope 120 of the present embodiment is described as a medical endoscope, the endoscope does not have to be limited thereto. The endoscope 120 may be an industrial endoscope to be inserted into an industrial conduit such as a pipe, or an insertion instrument such as a catheter having only an illumination optical system.

As shown in FIG. 13A, the endoscope 120 includes an elongated hollow insertion portion 121 that is to be inserted into a tract such as a lumen, and an operation portion 123 connected to the proximal end of the insertion portion 121 to operate the endoscope 120. The endoscope 120 includes a universal cord 125 connected to the operation portion 123 and extending from the side surface of the operation portion 123.

The universal cord 125 has a connection portion 125b attachable to and detachable from the image processing device 130 and the laser light source device 20. The connection portion 125b detachably connects the laser light source device 20 and the endoscope 120 to each other, and detachably connects the endoscope 120 and the image processing device 130 to each other. The connection portion 125b is provided for data transmission/reception between the endoscope 120 and the image processing device 130.

The image processing device 130 and the laser light source device 20 are electrically connected to each other (not shown).

As shown in FIG. 13A, the laser light source device 20 is provided separately from the endoscope 120, outside the endoscope 120.

As shown in FIG. 13B, the endoscope system 110 further includes a lighting apparatus 10 that emits the illumination light IL from the distal end of the insertion portion 121 to the outside.

The laser light source device 20 has a plurality of light sources. Hereinafter, these light sources are referred to as light sources 21V, 21B, 21G, and 21R. The light sources 21V, 21B, 21G, and 21R are mounted on a control board (not shown) that constitutes a light source controller 153 configured to individually control the light sources 21V, 21B, 21G, and 21R. The light source controller 153 is electrically connected to the controller 155. The controller 155 controls the entire endoscope system 110 including the endoscope 120, the display unit 140, and the laser light source device 20. The controller 155 may be arranged within the image processing device 130. The controller 155 is constituted by, for example, a hardware circuit including an ASIC or the like. The controller 155 may be constituted by a processor. If the controller 155 is configured by a processor, program codes may be stored in an internal memory in the processor or an external memory (not shown) that is accessible by the processor so that the processor can function as the controller 155 when the processor executes the program codes.

The light sources 21V, 21B, 21G, and 21R emit the primary lights PL having optically different wavelengths. The light sources 21V, 21B, 21G, and 21R may emit the primary lights PL having high coherence such as laser light.

The light source 21V may have a laser diode 22V that emits a purple laser beam. This laser beam may have a central wavelength of 405 nm.

The light source 21B may have a laser diode 22B that emits a blue laser beam. This laser beam may have a central wavelength of 445 nm.

The light source 21G may have a laser diode 22G that emits a green laser beam. This laser beam may have a central wavelength of 510 nm.

The light source 21R may have a laser diode 22R that emits a red laser beam. This laser beam may have a central wavelength of 630 m.

The laser diodes 22V, 22B, 22G, and 22R are arranged inside the housings 25V, 25B, 25G, and 25R of the respective light sources 21V, 21B, 21G, and 21R. In each of the housings 25V, 25B, 25G, and 25R, light collectors 23 such as lenses are provided.

Each of the light sources 21V, 21B, 21G, and 21R is optically connected to a multiplexer 157, which will be described later, via light guides 171a. Each of the light guides 171a may include a single core optical fiber. The primary lights PL emitted from the laser diodes 22V, 22B, 22G, and 22R are collected by the light collectors 23 to the single core light guides 171a. Then, the primary lights PL are guided to the multiplexer 157 by the light guides 171a. The light sources 21V, 21B, 21G, and 21R, the light source controller 153, the controller 155, and the single core light guides 171a are provided inside the laser light source device 20.

To provide white illumination, the light source 21B, the light source 21G, and the light source 21R are used. With four or more light sources as in the case of the light sources 21V, 21B, 21G, and 21R, white light observation using white light with high color rendering properties can be implemented. When the light source 21V and the light source 21G are used, special light observation adopting the light absorption characteristics of hemoglobin can be implemented. In this special light observation, blood vessels are displayed in a highlighted fashion. With the use of a light source that emits near-infrared light, observation using the near-infrared light can be implemented. The light source may be selected in accordance with the observation. According to the present embodiment, visible lights are adopted, but the light is not limited thereto.

As shown in FIG. 13B, the lighting apparatus 10 further includes the multiplexer 157 provided inside the laser light source device 20 to multiplex a plurality of primary lights PL emitted from the light sources 21V, 21B, 21G, and 21R into one light.

The multiplexer 157 allows the primary lights PL guided by the four light guides 171a to enter one light guide 171b. According to the present embodiment, the multiplexer 157 has four input ports and one output port. The number of input ports is equal to the number of light sources. The number of output ports is not particularly limited. At the input port, each of the light guides 171a has a thin optical fiber, and the light guides 171a are bundled together. At the output port, the light guide 171b has a thick optical fiber. This thick light guide 171b is thicker than the bundled light guide 171a. Fusion slicing is performed on the thick light guide 171b with the bundled light guides 171a so that the thick light guide 171b can be optically connected to the bundled light guides 171a. The multiplexer 157 functions as an optical combiner.

As shown in FIG. 13B, the lighting apparatus 10 further includes an optical branch 159 provided inside the laser light source device 20 to branch the primary light PL multiplexed by the multiplexer 157 into a plurality of primary lights PL.

The optical branch 159 allows the primary light PL guided by one light guide 171b to enter, for example, two optical fibers 50. According to the present embodiment, the optical branch 159 has one input port and two output ports. The number of input ports of the optical branch 159 is equal to the number of output ports of the multiplexer 157. The number of output ports is not particularly limited as long as it is more than one. That is, the number of optical fibers 50 should be plural. The optical branch 159 may branch the primary light PL at a desired ratio. According to the present embodiment, the ratio is 50:50. This ratio does not have to be even for the respective output ports. The optical branch 159 functions as a coupler.

In the structure of the optical branch 159, the light guide 171b is identical to one of the optical fibers 50. In other words, the light guide 171b and the optical fiber 50 function as the same member; for example, as the same optical fiber. The other optical fiber 50 is welded to this optical fiber 50, and the welded portion is further fused and drawn. In this manner, the primary light PL can be delivered and received between the light guide 171b and the other optical fiber 50.

According to the present embodiment, the input port of the optical branch 159 is optically connected to the output port of the multiplexer 157. As a result, the primary light PL input to the optical branch 159 may be branched into two optical fibers 50 at a ratio of 50:50.

When the optical branch 159 is provided in the laser light source device 20 as shown in FIG. 13B, the light guide 171b is provided inside the laser light source device 20, and the optical fibers 50 are provided inside the laser light source device 20 and inside the endoscope 120.

A plurality of single core optical fibers 50 are provided independently from each other, and the optical fibers 50 are single wires of mutually different systems. That is, the optical fibers 50 have the same optical function of guiding light, but are separate members. The single core optical fibers in the light guides 171a and 171b are single wires of different systems. In other words, the optical fibers have the same optical function of guiding light, but are separate members.

As shown in FIG. 13B, when the optical branch 159 is provided in the laser light source device 20, the optical fiber 50 provided in the laser light source device 20 is a separate member from the optical fiber 50 provided on the side of the connection portion 125b.

The method of optically connecting the optical fiber 50 provided on the side of the laser light source device 20 to the optical fiber 50 provided on the side of the connection portion 125b shown in FIG. 13B will be briefly described.

The laser light source device 20 and the connection portion 125b are each provided with a plug unit 191. The optical fiber 50 provided in the laser light source device 20 is inserted into the plug unit 191 on the side of the laser light source device 20. The optical fiber 50 provided on the side of the connection portion 125b is inserted into the plug unit 191 on the side of the connection portion 125b.

As shown in FIG. 13B, the laser light source device 20 has an optical adapter 193 fixed to the laser light source device 20. The plug unit 191 on the side of the laser light source device 20 is attached to the optical adapter 193 in advance. When the connection portion 125b is connected to the laser light source device 20, the plug unit 191 on the side of the connection portion 125b is inserted into the optical adapter 193. As a result, the optical fiber 50 on the side of the laser light source device 20 is optically connected to the optical fiber 50 on the side of the connection portion 125b. The plug unit 191 on the side of the connection portion 125b is attachable to and detachable from the optical adapter 193 of the laser light source device 20.

The primary light PL is emitted from each of the laser diodes 22V, 22B, 22G, and 22R, and is collected to the light guide 171a by the light collector 23. The primary lights PL are guided to the multiplexer 157 by the light guides 171a, where they are multiplexed by the multiplexer 157. The multiplexed primary light PL is guided to the optical branch 159 by the light guide 171b, and branched by the optical branch 159. The branched primary lights PL are guided to the light converters 60 by the optical fibers 50.

The primary light PL, which is a laser light having a very narrow light distribution and high directivity, is incident on the diffusing structure 61 of the light converter 60, and the diffusing structure 61 diffuses the primary light PL. If the diffusing structure 61 is formed, for example, on the center axis C of the core 51, the diffusing structure 61 diffuses part of the primary light PL. If the diffusing structure 61 is formed, for example, only inside the core 51 or inside the core 51 and the cladding 53, the diffusing structure 61 diffuses all the primary light PL guided by the optical fiber 50. Thus, the diffusing structure 61 diffuses at least part of the primary light PL. Due to the diffusion phenomenon, the backward illumination light BIL and the forward illumination light FIL having a reduced directivity and a wide light distribution are generated.

The backward illumination light BIL is guided to the optical branch 159 by the optical fiber 50, multiplexed by the optical branch 159 which is provided with the function of the multiplexing section also, and guided to the multiplexer 157 by the light guide 171b. The backward illumination light BIL is branched by the multiplexer 157 which is provided with the function of the branching section also, and returned to the light sources 21V, 21B, 21G, and 21R by the light guides 171a. As described above, the backward illumination light BIL is guided in the direction opposite to the direction of the primary light PL so as to travel through the optical fiber 50 and the light guides 171b and 171a in a reverse direction with respect to the traveling direction of the primary light PL, and to return to the light sources 21V, 21B, 21G, and 21R.

The backward illumination light BIL is collected by the light collector 23 to the laser diode 22V, 22B, 22G, or 22R at the light source 21V, 21B, 21G, or 21R. The laser diodes 22V, 22B, 22G, and 22R absorb the backward illumination light BIL, and convert the absorbed backward illumination light BIL into heat. This heat is released to the outside. The outside indicates, for example, the external environment of the laser light source device 20 or the atmosphere inside the laser light source device 20.

The laser diodes 22V, 22B, 22G, and 22R convert the backward illumination light BIL to heat at positions away from the light converter 60 of the lighting unit 40 and release the heat at positions away from the light converter 60. For this reason, according to the present embodiment, the heat generated at the time of illumination from the distal end portion of the insertion portion 121, in which the light converter 60 is provided, can be minimized.

In the forward illumination light FIL, the diffusion lowers the strong directivity of the primary light PL, and widens the distribution of the illumination light IL. At the exit end 70, the forward illumination light FIL is emitted only from the end surface emitting structure 71 (e.g., from the distal end surface 51c of the core 51) as shown in FIG. 2, or emitted from the end surface emitting structure 71 and the peripheral surface emitting structure 73 (i.e., the cutout portion 73a and the outer peripheral surface of the core 51) as shown in FIGS. 12A, 12B, 12C and 12D. The forward illumination light FIL is incident on an illumination target area (not shown). Here, the diffusion realizes the illumination light IL in a safe manner for the user of the endoscope system 110 having the lighting unit 40 and the endoscope 120, and reduces the speckle, which is a phenomenon peculiar to laser light.

The present embodiment is not directed to a diffuser arranged as a component separate from the optical fiber on the distal end surface of the optical fiber to generate the illumination light IL. According to the present embodiment, the light converter 60 that generates the illumination light IL is formed inside the optical fiber 50, and the exit end 70 functions as the end portion of the optical fiber 50. That is, the light converter 60 and the exit end 70 are part of the optical fiber 50, and are uniformly formed with the optical fiber 50. With such a structure, even if various thermal, physical, or chemical loads are externally applied to the lighting unit 40, the light converter 60 and the exit end 70 will not come off the optical fiber 50 under such loads. Thus, the primary light PL that is the laser light can be reliably diffused, and the laser light can be prevented from being emitted to the outside as is, allowing the diffused light to be used as illumination light IL having a wide light distribution. The present embodiment offers a lighting unit 40 that can obtain high reliability against an externally applied load. The light converter 60 and the exit end 70 are part of the optical fiber 50, for which the single core optical fiber 50 is used. Therefore, the number of components of the lighting unit 40 can be reduced, which offers the insertion portion 121 with a small thickness. For the optical fiber 50, a single core optical fiber is adopted instead of a fiber bundle, or one optical fiber in a fiber bundle. This can reduce the thickness of the insertion portion 121.

The light converter 60 is formed inside the core 51 of the optical fiber 50 that guides the primary light PL, or inside the core 51 and the cladding 53. With such a structure, at least part of the optical properties of the primary light PL can be reliably converted, and thus the illumination light IL can be reliably generated.

In general, the intensity of the primary light PL is higher on the center axis C of the core 51 and lower further away from the center axis C of the core 51 in the radial direction of the core 51. According to the present embodiment, at least part of the light converter 60 formed on the center axis C of the core 51 provides the illumination light IL having a uniform intensity and a symmetrical light distribution at the exit end 70 (the distal end surface 51c of the core 51).

Furthermore, the multimode optical fiber 50 can increase the light distribution angle of the guided light. Therefore, even without any diffusing structure 61, the illumination light IL having a wide light distribution angle that is defined by the NA uniquely determined for the optical fiber 50 can be emitted. According to the present embodiment, the light converter 60 generates the secondary light (illumination light IL) that is emitted with a light distribution angle larger than or equal to the NA of the optical fiber 50. Therefore, the secondary light (illumination light IL) with a still larger light distribution angle can be emitted.

When the light distribution angle of the illumination light IL becomes larger than the NA of the optical fiber 50, part of the illumination light IL tends to leak through the cladding 53 in the optical fiber 50 before it reaches the exit end 70. According to the present embodiment, however, by configuring the light converter 60 to satisfy the expression (3), the secondary light (illumination light IL) having a light distribution angle larger than the NA of the optical fiber 50 can be reliably guided to the exit end 70, without leaking through the cladding 53 to the outside of the optical fiber 50, and be emitted to the outside of the optical fiber 50 from the exit end 70 only. The amount of illumination light IL that is wasted can be reduced, allowing most of the illumination light IL to be useful.

The light converter 60 has a diffusing structure 61, which has a refractive index different from the refractive index of the core 51. Thus, according to the present embodiment, there will always be a difference in refractive index at the interface between the diffusing structure 61 and the core 51, which can reliably diffuse the primary light PL and generate the illumination light IL (diffused light) having a wide light distribution.

According to the present embodiment, the diffusing structure 61 can be fabricated with speed and at reduced cost by laser processing. The light distribution of the illumination light IL can be adjusted in accordance with the position, refractive index, shape and size of the diffusing structure 61, and the intensity distribution of the illumination light IL can be adjusted at the exit end 70 (distal end surface 51c of the core 51).

The number of diffusing structures 61 is not particularly limited. A plurality of diffusing structures 61 may be arranged in the direction of the center axis C of the core 51, as shown in FIG. 6. In this manner, the number of diffusions can be adjusted, and the light distribution angle of the illumination light IL can be adjusted, which offers the illumination light IL having a still larger light distribution angle. In addition, the intensity distribution of the illumination light IL can be adjusted at the exit end 70 (the distal end surface 51c of the core 51). The densities of the diffusing structures 61 may differ from each other. For example, as shown in FIG. 6, the density of the first diffusing structure 61a is higher or lower than the density of the second diffusing structure 61b. The light distribution angle of the illumination light IL can be adjusted based on the difference in density, and the intensity distribution of the illumination light IL can be adjusted.

For example, a plurality of diffusing structures 61 may be arranged in a vertical cross section as shown in FIG. 7. The third diffusing structure 61*c* may be arranged on the center axis C of the core 51, and the fourth diffusing structure 61*d* having a lower density than the third diffusing structure 61*c* may be arranged in the periphery of the center axis C of the core 51. In general, the intensity of the primary light PL is higher on the center axis C of the core 51 and lower further away from the center axis C of the core 51 in the radial direction of the core 51. According to the present embodiment, the third and fourth diffusing structures 61*c* and 61*d* form the illumination light IL with a uniform intensity and a symmetrical light distribution at the exit end 70 (the distal end surface 51*c* of the core 51). As illustrated in FIGS. 8A and 8B, the third diffusing structure 61*c* may be arranged on the front side of the longitudinal cross section S2, while the fourth diffusing structure 61*d* may be arranged on the back side of the longitudinal cross section S2. Alternatively, as illustrated in FIGS. 8C and 8D, one diffusing structure 61 may be arranged on the front side of the longitudinal cross section S2. In this manner, the illumination light IL having a non-uniform intensity and an asymmetrical light distribution can be obtained in accordance with the positional relationship between the exit end 70 and the imaging device and the light receiving sensitivity of the imaging device.

The exit end 70 functions as the distal end surface of the optical fiber 50, and the distal end surface has the end surface emitting structure 71. When the end surface emitting structure 71 is a planar surface, the illumination light IL with a uniform intensity can be provided, and most of the illumination light IL can be used. When the end surface emitting structure 71 is in the shape of a lens, a wider light distribution can be efficiently realized, together with diffusion.

The exit end 70 may function as the outer peripheral surface of the optical fiber 50 between the distal end surface and the light converter 60, and the outer peripheral surface has a peripheral surface emitting structure 73. Therefore, the illumination light IL with a wide light distribution can be provided.

As shown in FIG. 14, the light converter 60 may be provided with a light converting member 65 that converts at least part of the optical properties of the primary light PL. For example, the light converting member 65 is arranged in a hole 55 that passes through the core 51 and the cladding 53 in a collinear manner. The light converting member 65 may be inserted into the hole 55 without gaps, or may be arranged in part of the hole 55. The hole 55 may be formed by laser processing.

The light converting member 65 may be transparent. The light converting member 65 may include one or more diffusing members 65*a* that diffuse at least part of the primary light PL and/or one or more wavelength converting members 65*b* that convert the wavelength of at least part of the primary light PL. In addition, the light converting member 65 may have a containing member 65*c* that includes the diffusing member 65*a* and/or the wavelength converting member 65*b* that are the components of the light converting member 65. The members 65*a* and 65*b* of the light converting member 65 are dispersed inside the containing member 65*c*, and sealed by the containing member 65*c*.

The diffusing member 65*a* may be fine particles formed by, for example, a metal or a metal compound. The diffusing member 65*a* may be alumina, titanium oxide, or barium sulfate. The particle size of the diffusing member 65*a* is several hundred nanometers to several tens of micrometers. The diffusing member 65*a* has a refractive index different from the refractive index of the containing member 65*c*. For example, the refractive index of the diffusing member 65*a* may be preferably higher than the refractive index of the containing member 65*c*. The diffusing member 65*a* can thereby improve the diffusibility of the primary light PL.

The wavelength converting member 65*b* absorbs the primary light PL and generates light (for example, fluorescence) having a wavelength different from that of the primary light PL. The wavelength converting member 65*b* may be fluorescent particles. Given that the generated fluorescence travels in any directions in addition to the forward direction, the wavelength converting member 65*b* may be considered as a diffusing member 65*a* in a broad sense.

The containing member 65*c* is formed by a member through which the primary light PL can pass. Such a containing member 65*c* may be a transparent silicone resin or a transparent epoxy resin. The containing member 65*c* exhibits a high transmittance with respect to the primary light PL. The containing member 65*c* seals the contained members.

The light distribution angle of the light converting member 65 may be controlled by the concentration of the diffusing member 65*a* and/or the wavelength converting member 65*b* with respect to the containing member 65*c*, and the thickness of the light converting member 65.

According to the present embodiment, the light converting member 65 may further widen the light distribution angle of the illumination light IL. In addition, when the light converting member 65 is arranged in part of the hole 55, part of the primary light PL may be diffused at the interface between the hole 55 and the core 51, while the remaining part of the primary light PL is subjected to the diffusion or wavelength conversion by the light converting member 65. That is, the optical properties of the primary light PL may be subjected to the conversion twice. This can further widen the light distribution angle of the illumination light IL. The light converting member 65 may be arranged in an approximately columnar diffusing structure 61 that runs through the core 51 and the cladding 53 in a collinear manner (see FIG. 3).

The containing member 65*c* may be omitted, and the diffusing member 65*a* and/or the wavelength converting member 65*b* that is a fluorescent substance may be arranged in the hole 55. In addition, the diffusing member 65*a* may be arranged in the hole 63*a* with the diffusing member 65*a* stacked on the wavelength converting member 65*b*.

The endoscope 120 may be of a wireless type (not shown). If this is the case, the endoscope 120 is of a wireless type in which a radio signal is transmitted and received between the operation portion 123 and the image processing device 130.

The lighting apparatus 10 is therefore provided in the wireless type endoscope 120, and the light sources 21V, 21B, 21G, and 21R are arranged inside the operation portion 123. Furthermore, the endoscope 120 includes a wireless unit (not shown) for receiving wireless signals output from the image processing device 130, and a controller (not shown) for controlling the light sources 21V, 21B, 21G, and 21R based on the wireless signals received by the wireless unit. The wireless unit and the controller may be arranged inside the operation portion 123. The endoscope 120 has a supply unit (not shown) that supplies energy to the wireless unit, the controller, and the light sources 21V, 21B, 21G, and 21R, and a multiplexing/branching unit (not shown). The supply unit may include a battery for supplying energy that is electric power. The supply unit also supplies energy to every member of the endoscope 120. The supply unit and the multiplexing/branching unit are arranged inside the operation portion 123. The multiplexing/branching unit has the functions of the multiplexer 157 and the optical branch 159. The multiplexing/branching unit functions as an optical combiner and a coupler. The multiplexing/branching unit is connected optically to the light sources 21V, 21B, 21G, and 21R via respective light guide members (not shown). The multiplexing/branching unit multiplexes the primary lights PL emitted respectively from the light sources 21V, 21B, 21G, and 21R. The multiplexing/branching unit is optically connected to the optical fibers 50 arranged in the insertion portion 121. The multiplexing/branching unit branches the multiplexed primary light so as to correspond to the number of optical fibers 50. The multiplexing/branching unit branches the primary light PL at a desired ratio. If two optical fibers 50 are arranged, the ratio may be 50:50. The ratio need not be uniform for these optical fibers 50.

In the same manner, the light sources 21V, 21B, 21G, and 21R may be arranged inside the operation portion 123 in the endoscope 120 of a wired type shown in FIG. 13B.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A lighting unit comprising:
   a single core optical fiber including an incident end and a distal end, the single core optical fiber being configured to guide primary light, which is a laser light incident on the incident end, to the distal end;
   a light converter formed into a shape determined in accordance with an energy density of the primary light, the light converter having a size smaller than or equal to a wavelength of the primary light and embedded at a position inside the optical fiber, the position being proximal to the distal end, the light converter being configured to, convert optical properties of at least part of the primary light guided by the optical fiber and generate secondary light; and
   an exit end arranged at the distal end of the optical fiber, the exit end being configured to emit the secondary light externally as illumination light.

2. The lighting unit according to claim 1, wherein
   the optical fiber includes a core and a cladding arranged on a periphery of the core, and
   the light converter is formed one of inside the core and inside the core and the cladding.

3. The lighting unit according to claim 2, wherein
   at least part of the light converter is formed on a center axis of the core, and
   the light converter generates the secondary light in a manner as to be emitted at a light distribution angle larger than or equal to an NA of the optical fiber.

4. The lighting unit according to claim 3, wherein
   L satisfies an expression indicated below, where d denotes a radius of the core, NA denotes an acceptable angle at which the optical fiber accepts the secondary light, n denotes a refractive index of external space of the optical fiber, and L denotes a distance between the exit end and the position where the light converter is formed:

$$L \le \frac{d \times n \times \sqrt{1 - \left(\frac{NA}{n}\right)^2}}{NA}$$

5. The lighting unit according to claim 1, wherein
   the light converter includes at least one diffusing structure configured to diffuse at least part of the primary light to generate the secondary light, and
   the diffusing structure has a refractive index different from a refractive index of an adjacent member with which the diffusing structure is in close contact.

6. The lighting unit according to claim 5, wherein
   the diffusing structure includes one of a hole, a refractive index modified portion having a refractive index higher than the refractive index of the adjacent member, an approximately spherical shape, approximately columnar shape, and a cracked portion.

7. The lighting unit according to claim 5, wherein
   the light converter includes one diffusing structure configured to diffuse at least part of the primary light to generate the secondary light,
   the optical fiber includes a core and a cladding arranged on a periphery of the core, and
   the diffusing structure is arranged on a front side of a vertical cross section including a center axis of the core center axis of the core.

8. The lighting unit according to claim 1, wherein
   the light converter includes a light converting member configured to convert the optical properties of at least part of the primary light.

9. The lighting unit according to claim 8, wherein
   the light converting member includes at least one of a diffusing member configured to diffuse at least part of the primary light, and a wavelength converting member configured to convert a wavelength of at least part of the primary light.

10. The lighting unit according to claim 1, wherein
    the exit end functions one of as a distal end surface of the optical fiber at the distal end, and as the distal end surface and an outer peripheral surface of the optical fiber between the distal end surface and the light converter.

11. The lighting unit according to claim 10, wherein
    the optical fiber includes a core and a cladding arranged on a periphery of the core, and
    the exit end includes an end surface emitting structure arranged in a distal end surface of the core at the distal end surface of the optical fiber and configured to emit the illumination light.

12. The lighting unit according to claim 11, wherein
    the end surface emitting structure includes one of a planar surface, a concaved lens that is concaved toward the incident end, a wedge form, a tapered pencil form, an uneven portion, and an anti-reflection coat.

13. The lighting unit according to claim 10, wherein
    the exit end includes a peripheral surface emitting structure arranged on the outer peripheral surface of the optical fiber between the distal end surface of the optical fiber and the light converter and configured to emit the illumination light from the outer peripheral surface of the optical fiber,
    the optical fiber includes a core and a cladding arranged on a periphery of the core, and the peripheral surface emitting structure includes a cutout portion that is arranged in the cladding and exposes an outer peripheral surface of the core.

14. The lighting unit according to claim 13, wherein the cutout portion is arranged one of in a ring form around the outer peripheral surface of the cladding, and in a dotted pattern around the outer peripheral surface of the cladding.

15. The lighting unit according to claim 13, wherein the peripheral surface emitting structure functions as the outer peripheral surface of the core that is exposed by removing the cladding.

16. A lighting unit comprising:
a single core optical fiber including an incident end and a distal end, the single core optical fiber being configured to guide primary light, which is a laser light incident on the incident end, to the distal end;
a light converter formed inside the optical fiber, the light convertor including a plurality of diffusing structures having densities that are different from one another and a refractive index that is different from a refractive index of an adjacent member with which the diffusion structures are in close contact the light converter being configured to diffuse at least part of the primary light guided by the optical fiber and generate the secondary light; and
an exit end arranged at the distal end of the optical fiber, the exit end being configured to emit the secondary light externally as illumination light.

17. The lighting unit according to claim 16, wherein
the plurality of diffusing structures include a first diffusing structure arranged near the exit end and a second diffusing structure arranged away from the exit end, and
a density of the first diffusing structure is one of higher that a density of the second diffusing structure, and lower than the density of the second diffusing structure.

18. The lighting unit according to claim 16, wherein the plurality of diffusing structures include a third diffusing structure and a fourth diffusing structure arranged in a cross section perpendicular to a center axis of the optical fiber, the fourth diffusing structure having a density lower than the third diffusing structure.

19. The lighting unit according to claim 18, wherein the optical fiber includes a core and a cladding arranged on a periphery of the core, and
the third diffusing structure is arranged on a center axis of the core in the perpendicular cross section, and the fourth diffusing structure is arranged in a periphery of the center axis.

20. The lighting unit according to claim 18, wherein the optical fiber includes a core and a cladding arranged on a periphery of the core, and
the third diffusing structure and the fourth diffusing structure are arranged symmetrically with respect to the vertical cross section including the center axis of the core.

* * * * *

UNITED STATES PATENT AND TRADEMARK OFFICE
CERTIFICATE OF CORRECTION

PATENT NO. : 10,598,850 B2
APPLICATION NO. : 16/183800
DATED : March 24, 2020
INVENTOR(S) : Satoshi Ohara It is certified that error appears in the above-identified patent and that said Letters Patent is hereby corrected as shown below:

On the Title Page

(71) Applicant should read:
OLYMPUS CORPORATION, Tokyo (JP)

Signed and Sealed this
Eleventh Day of August, 2020

Andrei Iancu
*Director of the United States Patent and Trademark Office*